(12) United States Patent
Kryscio et al.

(10) Patent No.: US 11,401,103 B2
(45) Date of Patent: Aug. 2, 2022

(54) DISPENSER APPARATUS AND METHOD OF USING SAME

(71) Applicant: Poka Yoke, Inc., Hinsdale, IL (US)

(72) Inventors: Renee Januchowski Kryscio, Hinsdale, IL (US); Kevin P. Kryscio, Hinsdale, IL (US)

(73) Assignee: Poka Yoke, Inc., Hinsdale, IL (US)

( * ) Notice: Subject to any disclaimer, the term of this patent is extended or adjusted under 35 U.S.C. 154(b) by 0 days.

(21) Appl. No.: 15/916,806

(22) Filed: Mar. 9, 2018

(65) Prior Publication Data

US 2018/0194540 A1    Jul. 12, 2018

Related U.S. Application Data

(63) Continuation-in-part of application No. 15/122,514, filed as application No. PCT/US2016/049220 on Aug. 29, 2016, now abandoned.

(Continued)

(51) Int. Cl.
*B65D 83/08* (2006.01)
*A47K 10/38* (2006.01)
(Continued)

(52) U.S. Cl.
CPC ...... *B65D 83/0805* (2013.01); *A47K 10/3827* (2013.01); *A61M 5/14* (2013.01); *B65D 25/22* (2013.01); *B65D 83/0864* (2013.01); *B65D 85/672* (2013.01); *A47K 2010/3233* (2013.01); *A47K 2010/3266* (2013.01)

(58) Field of Classification Search
CPC ...... A47K 10/22; A47K 10/38; A47K 10/426; A47K 10/3827; A47K 2010/389; A47K 2010/3233; B65D 2575/3281
See application file for complete search history.

(56) References Cited

U.S. PATENT DOCUMENTS 3,046,984 A * 7/1962 Eby .................. A61M 25/02
128/DIG. 26
3,315,910 A * 4/1967 Galley .............. A47K 10/3827
242/598.6

(Continued)

FOREIGN PATENT DOCUMENTS

WO    WO2012010902 A1    1/2012

OTHER PUBLICATIONS

International Search Report for International Application No. PCT/US16/49220, dated Feb. 1, 2017.

*Primary Examiner* — Gene O Crawford
*Assistant Examiner* — Kelvin L Randall, Jr.
(74) *Attorney, Agent, or Firm* — Ashley Law Firm P.C.; Stephen S. Ashley, Jr.

(57) ABSTRACT

A dispensing apparatus comprises a generally cylindrical housing, and attachment means adapted for attaching the housing to a support structure, such as an intravenous tubing line. The housing can contain a plurality of planar, interconnected items that are rolled up into a single roll. The interconnected items can be a plurality of individually packaged items, such as sanitizing wipes, in which each individual package is attached to another individual package along a line of perforation. A rolling mechanism can be mounted in the housing that supports the roll of wipes thereon and facilitates rotation of the roll.

18 Claims, 27 Drawing Sheets

Related U.S. Application Data

(60) Provisional application No. 62/211,148, filed on Aug. 28, 2015.

(51) Int. Cl.
  *A61M 5/14* (2006.01)
  *B65D 85/672* (2006.01)
  *B65D 25/22* (2006.01)
  *A47K 10/32* (2006.01)

(56) References Cited

U.S. PATENT DOCUMENTS

| | | | | |
|---|---|---|---|---|
| 3,533,533 A * | 10/1970 | Chaney, Jr. | | A47K 10/34 206/812 |
| 3,568,635 A * | 3/1971 | Poitras | | A61F 15/002 118/122 |
| 3,775,801 A * | 12/1973 | Walker | | A47K 10/3827 118/122 |
| 3,881,753 A * | 5/1975 | Bochory | | F16B 2/245 285/82 |
| 3,948,455 A * | 4/1976 | Schwartz | | B65D 83/0847 242/594.2 |
| 3,995,582 A | 12/1976 | Douglas | | |
| 4,034,926 A * | 7/1977 | Wegner | | B65D 85/672 206/406 |
| 4,082,094 A * | 4/1978 | Dailey | | A61M 39/1011 128/DIG. 26 |
| 4,114,780 A * | 9/1978 | Sharon | | B65D 83/10 206/359 |
| 4,221,449 A * | 9/1980 | Shugart, Jr. | | H01R 13/6392 439/369 |
| 4,328,907 A | 5/1982 | Beard | | |
| D302,304 S * | 7/1989 | Kulle | | D24/129 |
| D323,390 S * | 1/1992 | Paine | | D24/129 |
| 5,245,729 A * | 9/1993 | Greff | | F16G 11/046 24/129 R |
| 5,259,587 A | 11/1993 | D'Alessio et al. | | |
| 5,311,986 A | 5/1994 | Putz | | |
| 5,439,521 A * | 8/1995 | Rao | | A47K 10/3827 118/415 |
| 5,656,282 A | 8/1997 | Cook et al. | | |
| 5,660,313 A * | 8/1997 | Newbold | | A47K 10/32 206/205 |
| 5,810,781 A * | 9/1998 | Bierman | | A61M 25/02 128/DIG. 26 |
| 5,848,762 A * | 12/1998 | Reinheimer | | A47K 10/3827 242/595 |
| 5,897,074 A * | 4/1999 | Marino | | A47K 10/38 242/594.1 |
| 5,897,519 A * | 4/1999 | Shesol | | A61M 25/02 602/75 |
| 5,970,922 A * | 10/1999 | Lin | | A01K 27/001 119/867 |
| 6,151,722 A * | 11/2000 | Lubrano | | E03D 9/037 4/225.1 |
| 6,164,442 A * | 12/2000 | Stravitz | | A45C 3/02 206/233 |
| 6,240,881 B1 * | 6/2001 | Edwards | | A01K 27/004 119/795 |
| D464,179 S * | 10/2002 | Petersen | | D30/153 |
| 6,517,522 B1 * | 2/2003 | Bell | | A61M 25/0631 604/165.02 |
| 6,540,195 B2 | 4/2003 | Newman et al. | | |
| 6,763,776 B1 * | 7/2004 | Perri | | B63B 21/08 114/218 |
| D502,622 S * | 3/2005 | Berger | | D6/515 |
| 7,487,791 B1 * | 2/2009 | Bradley | | A61M 5/1418 137/355.16 |
| D616,233 S * | 5/2010 | Yang | | D6/518 |
| 7,850,039 B1 * | 12/2010 | Tsengas | | E01H 1/1206 206/409 |
| 8,511,511 B2 | 8/2013 | Thoren | | |
| 8,950,580 B2 | 2/2015 | Sharpe et al. | | |
| 8,967,523 B2 * | 3/2015 | Huang | | A47K 10/3827 242/402 |
| 9,033,154 B2 | 5/2015 | DeVore | | |
| 9,198,545 B2 * | 12/2015 | D'Angelo | | A47K 10/38 |
| 9,248,260 B2 * | 2/2016 | Khalaj | | A61M 25/02 |
| 9,604,034 B2 * | 3/2017 | Andino | | A61M 5/1418 |
| 2002/0096411 A1 * | 7/2002 | Tsuji | | B65H 75/4476 191/12 R |
| 2003/0116582 A1 | 6/2003 | Tosdale | | |
| 2004/0004013 A1 * | 1/2004 | Dleter | | A47K 10/3827 206/409 |
| 2005/0189372 A1 * | 9/2005 | Fenton | | A61F 5/08 221/231 |
| 2006/0150660 A1 * | 7/2006 | Heims | | F25D 23/126 62/389 |
| 2006/0213920 A1 | 9/2006 | Agarwal et al. | | |
| 2006/0237475 A1 | 10/2006 | Agarwal | | |
| 2007/0123841 A1 | 5/2007 | Egan et al. | | |
| 2007/0267531 A1 * | 11/2007 | Petersen | | B65D 83/0805 242/588.6 |
| 2008/0087560 A1 * | 4/2008 | Kelly | | A47K 10/422 206/229 |
| 2008/0097333 A1 * | 4/2008 | Henning | | A61M 5/1418 604/174 |
| 2008/0110919 A1 * | 5/2008 | Lincoln | | A47F 9/042 221/45 |
| 2010/0200706 A1 * | 8/2010 | Harding | | A61M 5/1415 248/62 |
| 2011/0024578 A1 | 2/2011 | Spiess et al. | | |
| 2012/0181297 A1 * | 7/2012 | Cofrancesco | | A47K 10/38 221/26 |
| 2013/0075416 A1 * | 3/2013 | Boyce | | A47K 10/38 221/34 |
| 2013/0081966 A1 | 4/2013 | DeVore | | |
| 2014/0291439 A1 * | 10/2014 | Winestock | | A47K 10/3827 242/588.3 |
| 2015/0157116 A1 * | 6/2015 | Williams | | A45F 5/004 224/162 |

* cited by examiner

DISPENSER APPARATUS AND METHOD OF USING SAME

CROSS REFERENCE TO RELATED APPLICATIONS

This application is a continuation-in-part of U.S. patent application Ser. No. 15/125,514, filed Aug. 30, 2016, which is a national stage application of International Application No. PCT/US2016/049220, filed Aug. 29, 2016, which claims priority to U.S. Provisional Patent Application No. 62/211,148, filed Aug. 28, 2015. All of said applications are incorporated herein by reference.

TECHNICAL FIELD OF INVENTION

The present invention relates to a dispensing apparatus. One embodiment of the invention comprises an apparatus adapted for dispensing sterile wipes, such as pads soaked in isopropyl alcohol, which can be mounted on an intravenous (IV) tubing line. Another embodiment of the invention comprises a dispenser apparatus that can be attached to a person's clothing. Another embodiment of the invention comprises a dispenser apparatus that can be attached to a lanyard worn by the user. Yet another embodiment of the invention comprises a dispenser apparatus that can be mounted on a wall.

BACKGROUND OF INVENTION

Healthcare professionals routinely use sanitizing wipes to clean and disinfect areas of a patient's body to prevent infections. For example, prior to insertion of an intravenous line into a patient, the healthcare professional typically wipes the area of the patient's body that is to be pierced with a pad soaked with a disinfectant liquid, such as isopropyl alcohol. Generally, such pads are individually wrapped and stored at various places, such as drawers and cabinets. A supply of the wipes is typically maintained in each room in which they are to be used, or else the healthcare professional must remember to bring a supply with him or her into the room in which they are to be used on the patient. If the supply of wipes runs out, or the healthcare professional forgets to have a supply on hand, the healthcare professional must leave the room or unlock a stocked cabinet to find a container of wipes. This can require the healthcare professional to spend valuable time away from the patient and delay urgent medical treatment. In addition, known sanitizing wipes are typically individually wrapped in packaging that generally requires two free hands to open. Due to the nature of medical treatment, it can be difficult and cumbersome for a healthcare professional to dedicate both hands to the task of opening the packaging and removing the pad from the packaging.

SUMMARY OF INVENTION

Therefore, one object of the present invention is to provide a dispensing apparatus that can dispense individually packaged items, such as sanitizing wipes, and can be attached to a support structure, such as medical equipment used by healthcare professionals. Another object of the present invention is to provide a dispensing apparatus, in which a user can remove an individually packaged wipe from its packaging using only one hand. These and other objects of the invention can be achieved in various embodiments of the invention described herein.

One embodiment of the invention comprises an apparatus for dispensing a plurality of applicator wipes comprising a generally cylindrical housing adapted for containing a roll of applicator wipes, and having a dispensing opening formed therein such that an applicator wipe contained in the housing can be grasped and pulled out of the housing. The apparatus includes attachment means for attaching the housing to a support structure, such as an intravenous (IV) tubing line, a lanyard or a wall.

According to another embodiment of the invention, a rolling mechanism is positioned within the interior of the housing, which facilitates rotation of the roll of applicator wipes.

According to another embodiment of the invention, the housing has first and second opposed longitudinal ends, and the rolling mechanism comprises a rod positioned in a first cavity positioned proximate the first end of the housing and a second cavity positioned proximate the second end of the housing.

According to another embodiment of the invention, the dispensing opening is defined by a dispensing lip extending outwardly from the housing. The dispensing lip comprises a first edge section and a second edge section in spaced apart relation and substantially parallel to the first edge section. The first and second edge sections define a slit sized to receive a single applicator wipe there through.

According to another embodiment of the invention, the dispensing opening is defined by a first cut away section formed in the housing. The first cut away section is in communication with the first edge section and defines a first exposed area of the housing that can receive a first finger of a user.

According to another embodiment of the invention, the dispensing opening is further defined by a second cut away section formed in the housing. The second cut away section is in communication with the second edge section and defines a second exposed area of the housing adapted for receiving a second finger of a user.

According to another embodiment of the invention, the attachment members can be releasably attached to a support structure, and the support structure can be an intravenous tubing line, a cord, a string, a snap fastener, or a wall.

According to another embodiment of the invention, the attachment means comprises at least one attachment member extending outwardly from the housing, and which defines an arcuate cavity sized and shaped to receive and releasably engage an intravenous tubing line.

According to another embodiment of the invention, the attachment means comprises at least one eyelet positioned on the housing.

According to another embodiment of the invention, the attachment means comprises at least one attachment member extending outwardly from the housing that is adapted for engaging a complimentary fastener attached to a wall.

Another embodiment of the invention comprises a dispensing apparatus comprising a generally cylindrical housing, and a roll of connected individual packages, in which each individual package is connected to another individual package along a line of perforation. A dispensing opening is formed in the housing and is adapted for dispensing one of the individual packages, and the housing includes at least one attachment member adapted for attaching the housing to a support structure.

According to another embodiment of the invention, the housing has first and second opposed longitudinal ends, and a rotatable rod is positioned in a first cavity positioned proximate the first end of the housing, and a second cavity positioned proximate the second end of the housing. The rotatable rod supports the roll of applicator wipes and facilitates rotation of the roll of applicator wipes.

According to another embodiment of the invention, each individual package contains a sanitizing wipe, antiseptic wipe, cleaning wipe, and/or moisturizing wipe.

According to another embodiment of the invention, the dispensing opening is defined by a dispensing lip extending outwardly from the housing, the dispensing lip comprising a first edge section and a second edge section in spaced apart relation and substantially parallel to the first edge section, the first and second edge sections defining a slit sized to receive one of the individual packages there through and facilitating tearing of the individual package along the line of perforation.

According to another embodiment of the invention, the dispensing opening is defined by a first cut away section formed in the housing. The first cut away section is in communication with the first edge section and defines a first exposed area exposing one of the individual packages contained within the housing, such that a user can place a first finger, such as a thumb, on one of the individual packages.

According to another embodiment of the invention, the dispensing opening is further defined by a second cut away section formed in the housing. The second cut away section is in communication with the second edge section and defines a second exposed area exposing one of the individual packages contained within the housing, such that a user can place a second finger, such as the user's index finger, on one of the individual packages.

According to another embodiment of the invention, first and second attachment members are positioned on the housing about 180 degrees from the dispensing opening. Each of the first and second attachment members include an arcuate cavity that is sized and shaped to receive and releasably engaging an intravenous tubing line.

According to another embodiment of the invention, the housing has first and second opposed longitudinal ends, and the attachment means includes a first eyelet positioned on the housing proximate the first longitudinal end and a second eyelet positioned on the housing proximate the second longitudinal end.

According to another embodiment of the invention, the apparatus includes a fastening device containing a retractable cord that is attached to an eyelet formed on the housing.

Another embodiment of the invention comprises a dispensing apparatus comprising a generally cylindrical housing comprising first and second body sections that are releasably attached to each other, and a roll of individual packages contained within the interior of the housing. The user can access the interior of the housing by disengaging the first and second body sections. A dispensing opening is formed in the housing through which the individual packages are dispensed.

Another embodiment of the invention comprises an apparatus for dispensing sanitizing wipes that is adapted for being mounted on an intravenous (IV) tubing line. The apparatus comprises a housing for containing sterile, sanitizing wipes and attachment means for attaching the housing to the IV tubing line. The attachment means can comprise a pair of attachment members positioned at opposite ends of the housing that can be attached to the IV tubing line. The housing contains a plurality of packaged, releasably attached sterile sanitizing wipes, such as isopropyl alcohol pads, that are rolled onto a rolling mechanism positioned within the housing. The housing includes a slit opening through which the pads can be pulled through.

According to another embodiment of the invention, the pads are perforated, and the first pad on the roll can be pulled through the slit opening and torn along the perforation line, thereby providing a single pad opened from its packaging and ready for use, leaving the remaining pads within the housing.

Another embodiment of the invention comprises an apparatus for dispensing wipes that is adapted to be attached to clothing worn by the user.

Another embodiment of the invention comprises a dispensing apparatus that is releasably attached to a lanyard that can be worn by the user.

Another embodiment of the invention comprises an apparatus for dispensing a plurality of applicator wipes comprising a generally cylindrical housing adapted for containing a roll of applicator wipes, the housing having a dispensing opening formed therein whereby an applicator wipe contained in the housing can be grasped and pulled out of the housing. First and second attachment members extend outwardly from the housing and are adapted to receive and frictionally engage an intravenous tubing line. A curved member is positioned intermediate the first and second attachment members and moves the intravenous tubing line at an angle relative to the first and second attachment members.

Another embodiment of the invention comprises a dispensing apparatus comprising a generally cylindrical housing adapted for containing a roll of applicator wipes, at least one attachment member extending outwardly from the housing adapted for receiving and frictionally engaging an intravenous tubing line, and a dispensing opening formed in the housing through which an applicator wipe contained in the housing can be grasped and pulled out of the housing. The dispensing opening comprises first and second edge sections in spaced apart relation and substantially parallel to each other. The first edge section and the second edge section define a slit sized to receive a single applicator wipe there through and are at least partially serrated to facilitate tearing of the single applicator wipe.

Another embodiment of the invention comprises a disposable dispensing apparatus comprising a generally cylindrical housing adapted for containing a roll of applicator wipes that is comprised of a first body section and a second body section. The first body section includes at least one tab member extending outwardly from the interior surface of the first body section, and the second body section has a complementary recessed section adapted to receive and engage the tab member such that the first body section and the second body section cannot be separated after being put together. A dispensing opening is formed in the housing for dispensing the applicator wipes, and at least one attachment member extends outwardly from the housing for attachment to a support structure.

DETAILED DESCRIPTION OF PREFERRED EMBODIMENTS OF INVENTION

Figure 8:
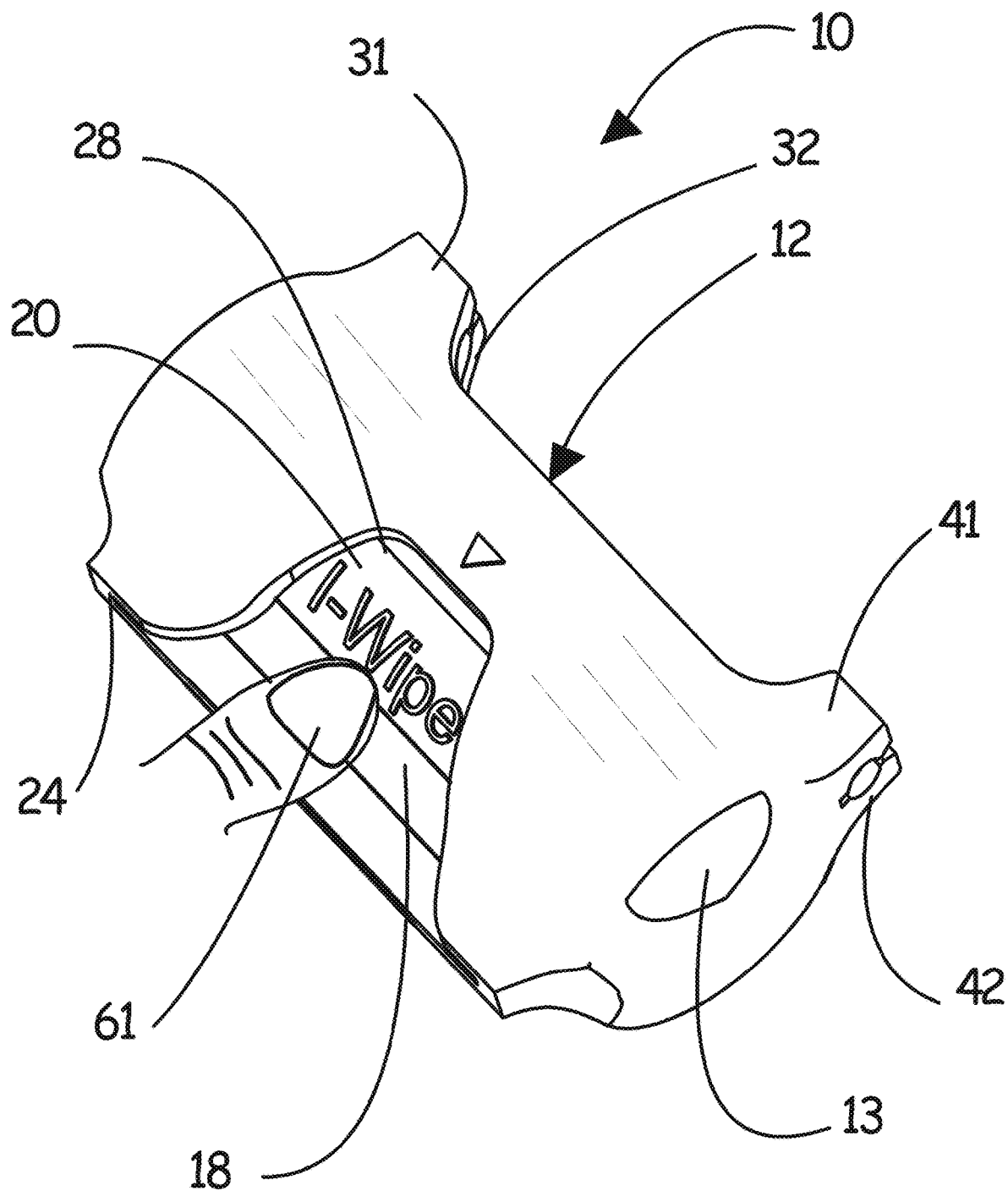
FIG. 8 is another perspective view of the dispenser apparatus of FIG. 1, shown including a roll of applicator wipes contained in the dispenser apparatus.
Figure 9:
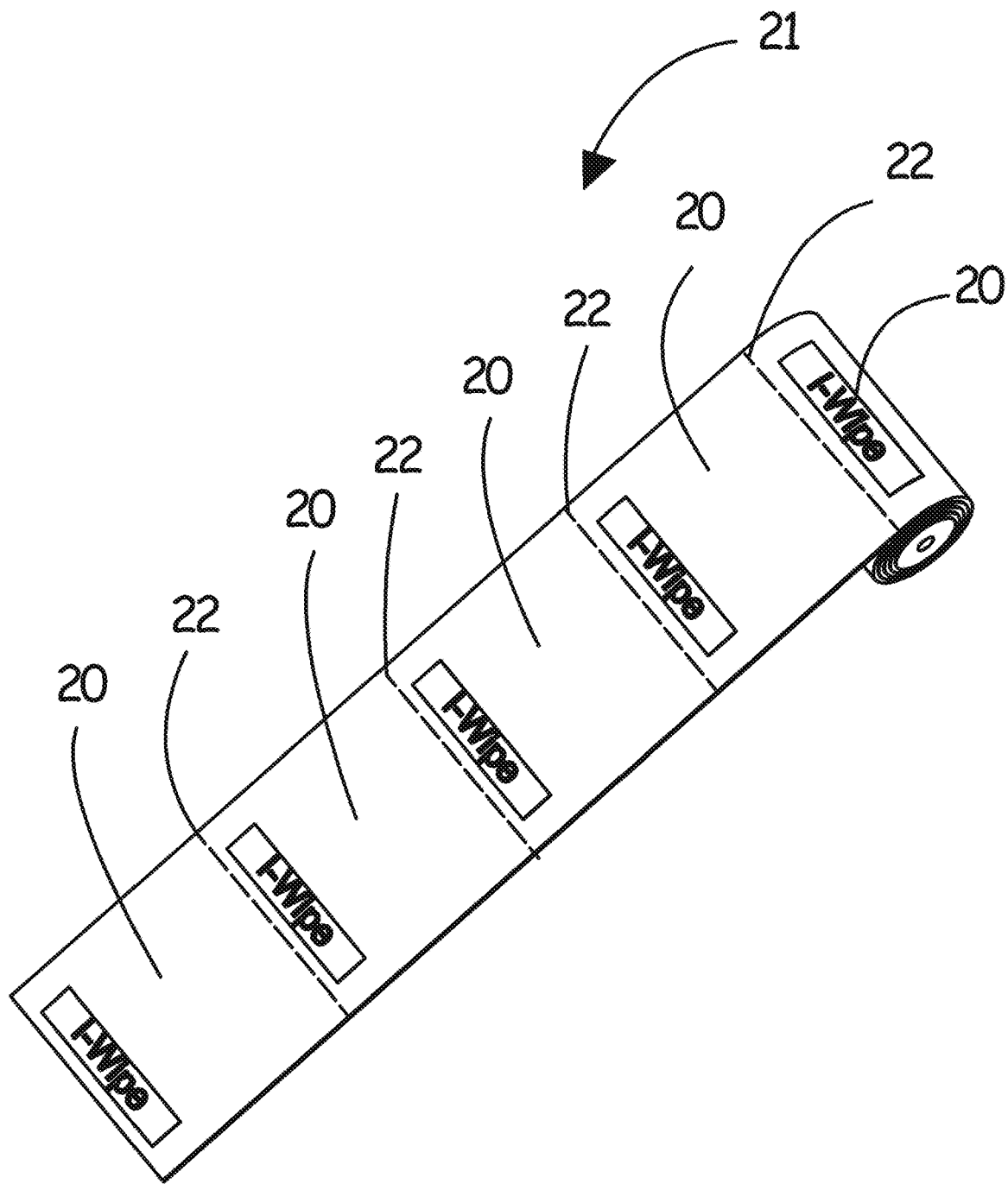
FIG. 9 is a perspective view of the roll of applicator wipes shown in FIG. 8.
Figure 10:
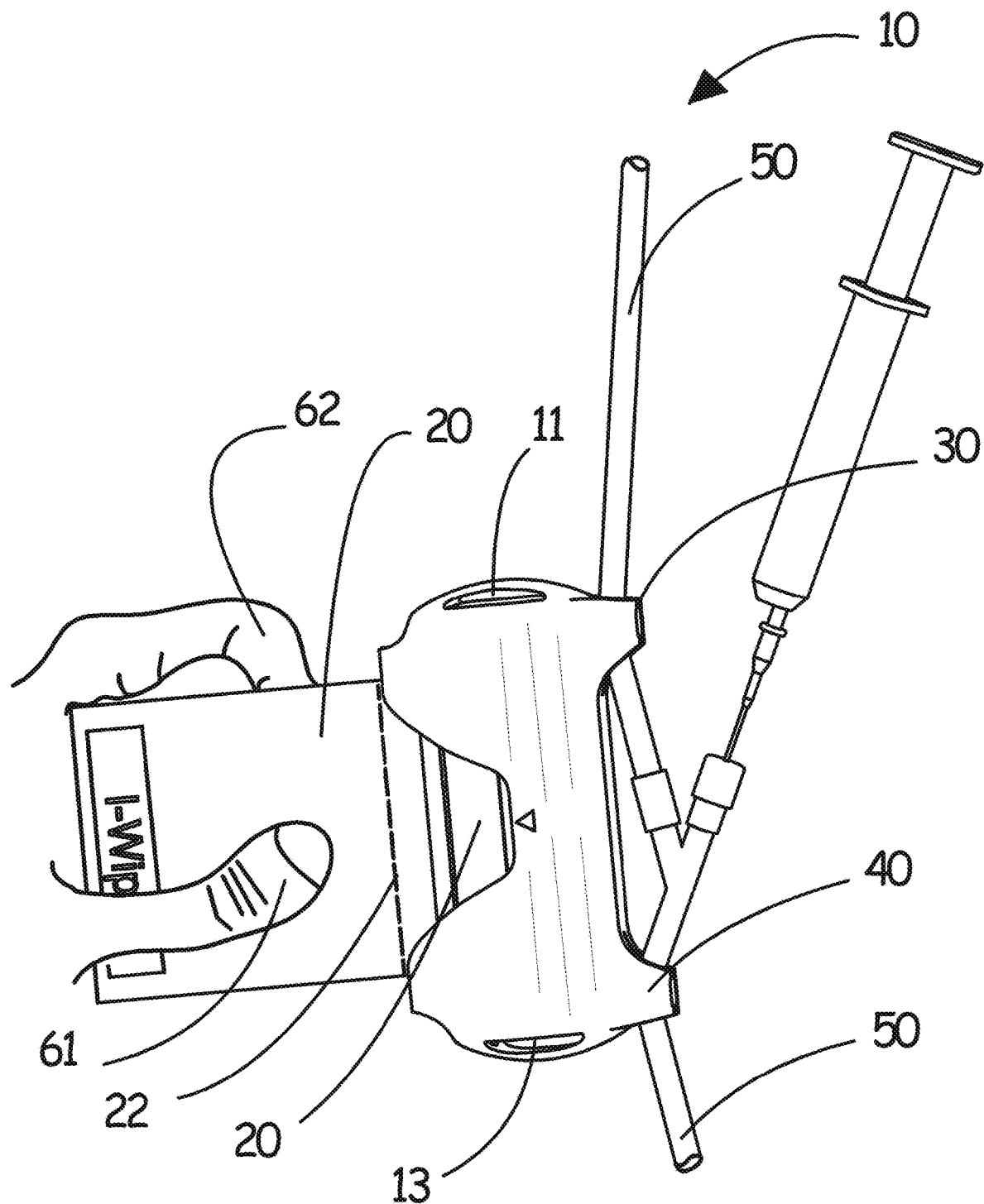
FIG. 10 is an environmental perspective view of dispenser apparatus of FIG. 1.

A dispenser apparatus according to a preferred embodiment of the invention is illustrated in FIGS. 1-11 and shown generally at reference numeral 10. The apparatus 10 comprises a substantially cylindrical housing 12, and attachment means adapted for attaching the housing 12 to a support structure, such as an intravenous (IV) tubing line 50, as shown in FIG. 10.

The housing 12 is adapted for containing a plurality of planar, interconnected items that are rolled up into a single roll. The interconnected items can be a plurality of individually packaged items, such as applicator wipes, in which each individual package is attached to another individual package along a line of perforation. As used herein, "applicator wipes" refers generally to any wipe, pad or like item made of paper, cloth, non-woven fibers or other suitable material that has been soaked, sprayed, bathed, saturated or otherwise treated with a liquid substance, such as a cleaning, sanitizing, disinfecting, or moisturizing solution, and can be used to apply the liquid substance to a person, animal or object.

Figure 4:
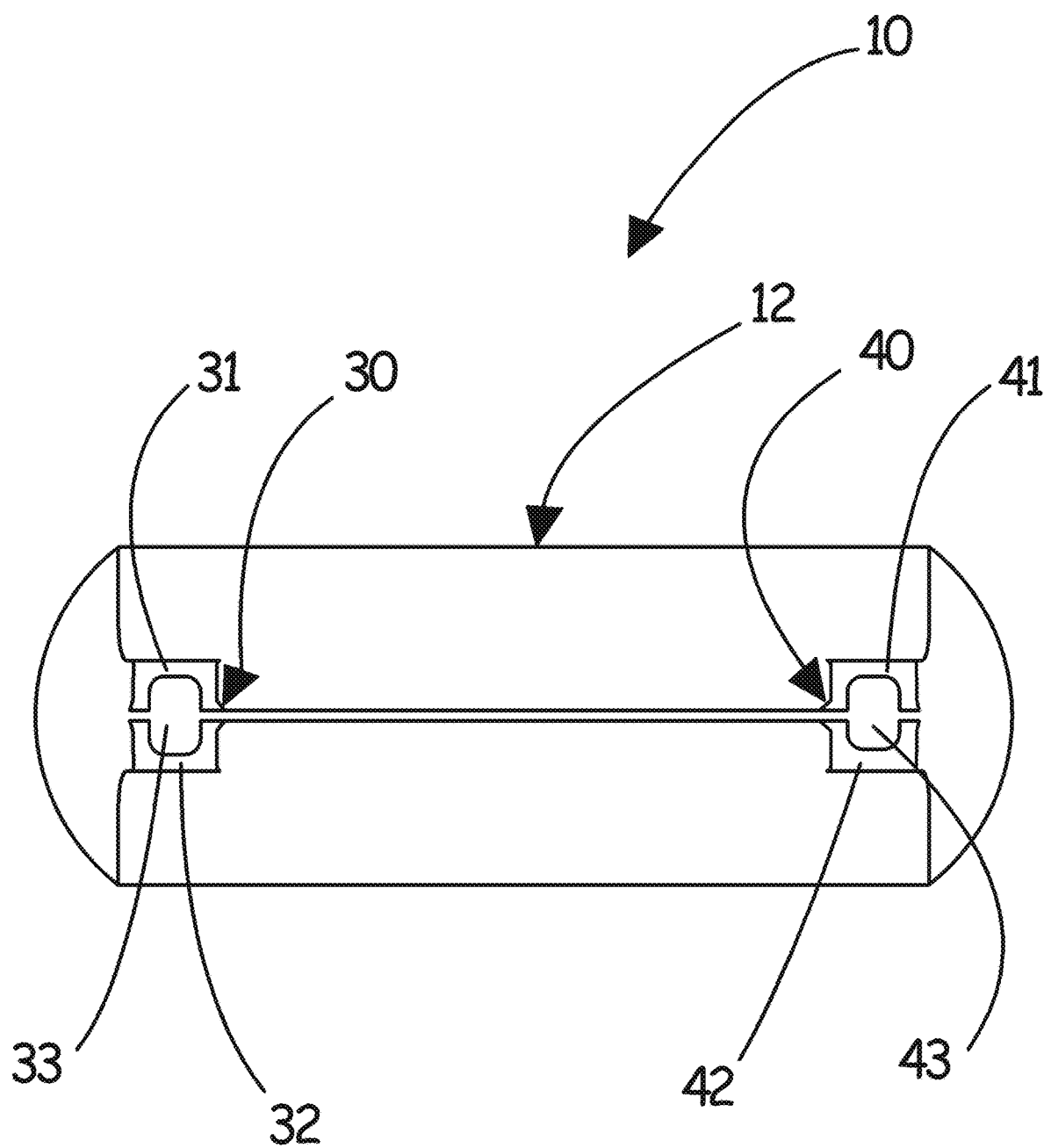
FIG. 4 is a rear view of the dispenser apparatus of FIG. 1.
Figure 5:
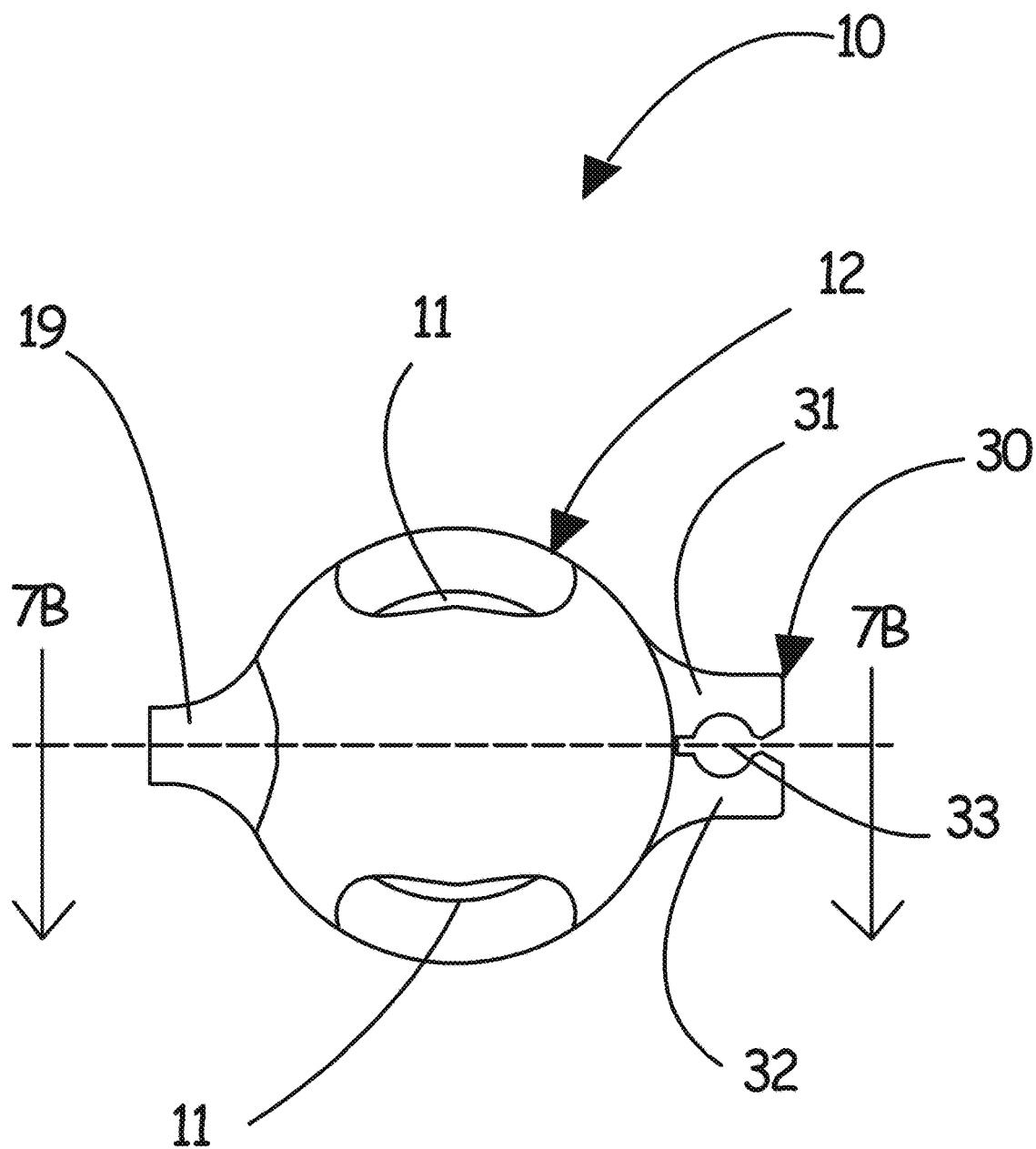
FIG. 5 is a side view of the dispenser apparatus of FIG. 1.
Figure 6:
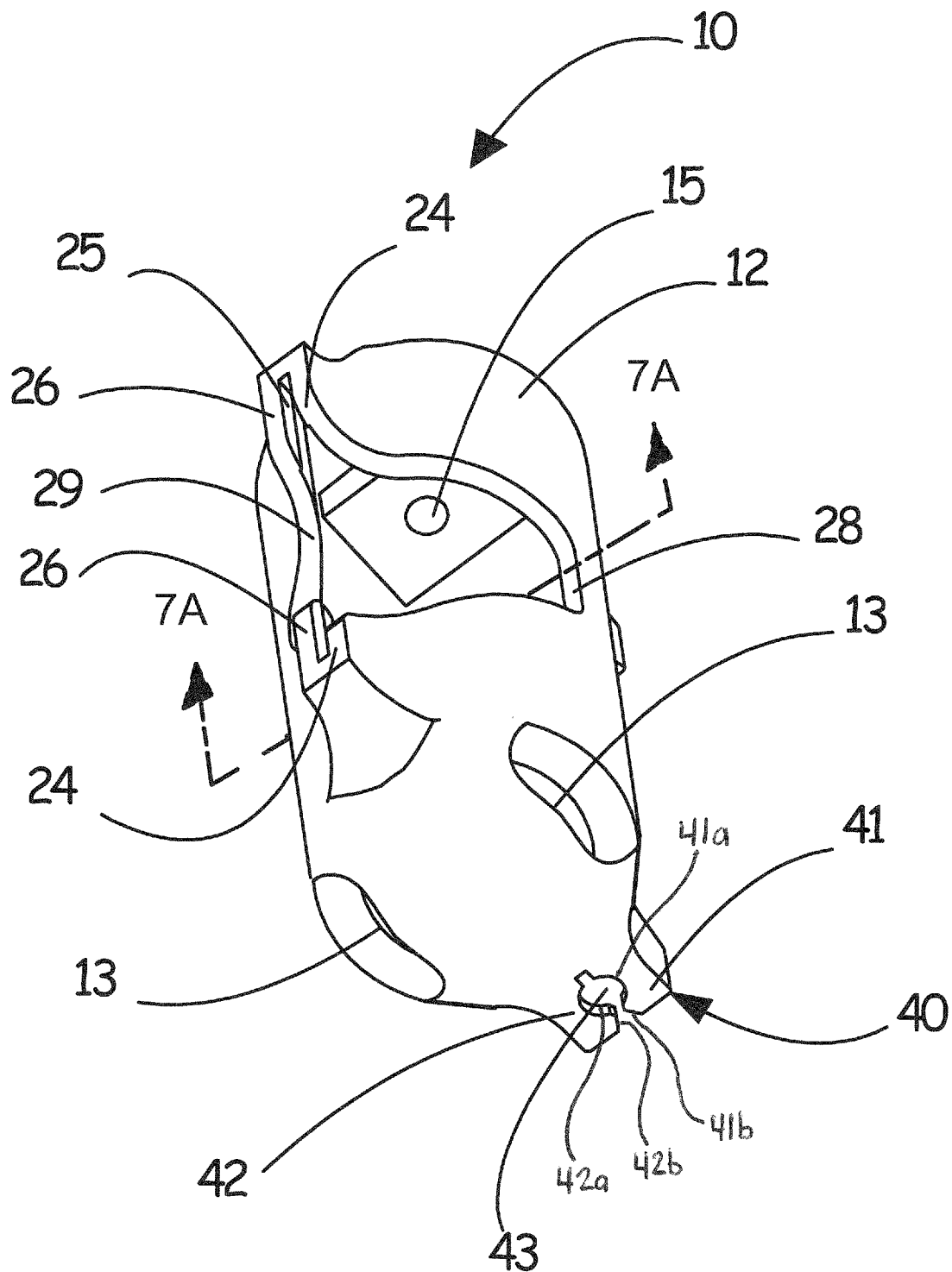
FIG. 6 is a perspective view of the dispenser apparatus of FIG. 1.
Figure 7A:
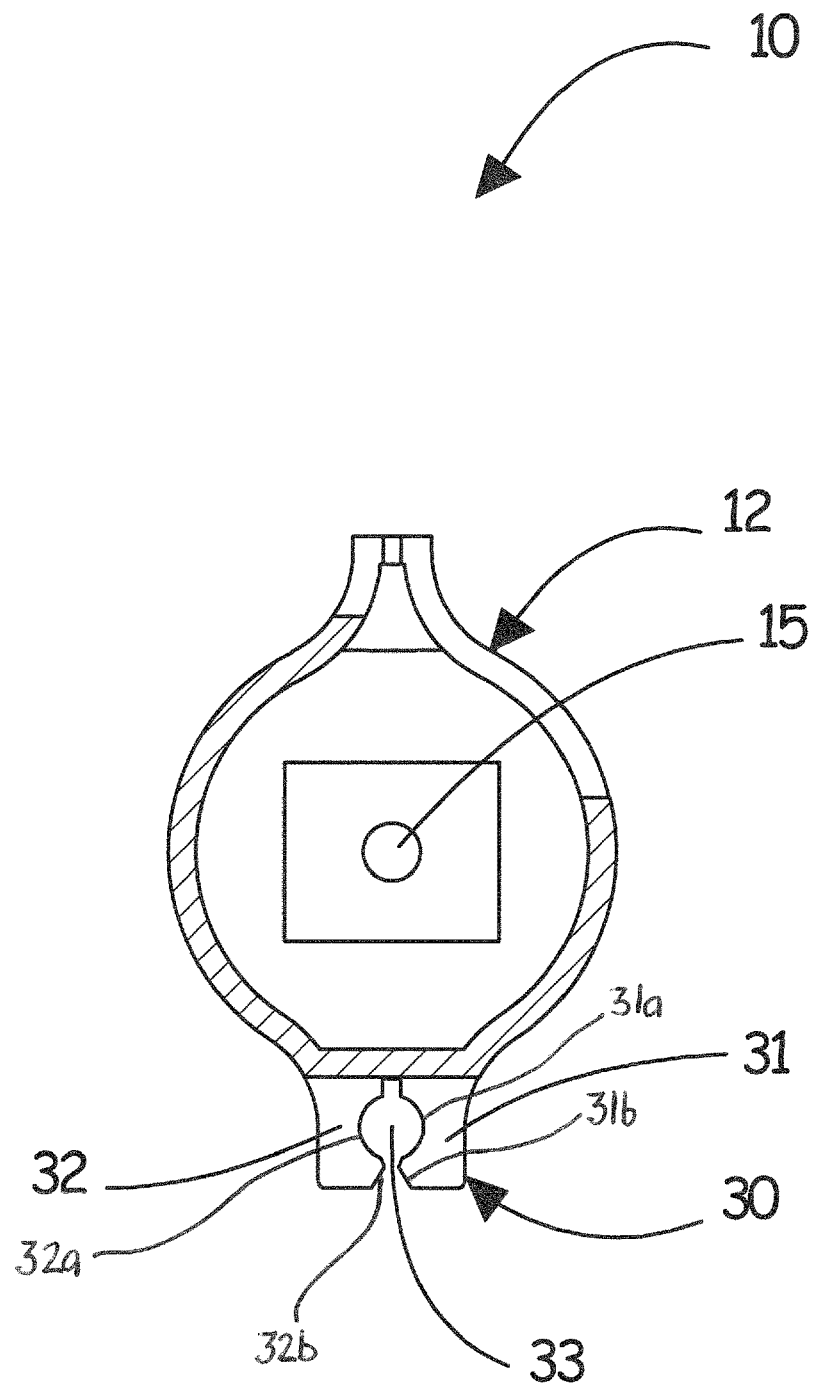
FIG. 7A is a cross sectional view of the dispenser apparatus of FIG. 1, taken along lines 7A-7A in FIG. 6.
Figure 11:
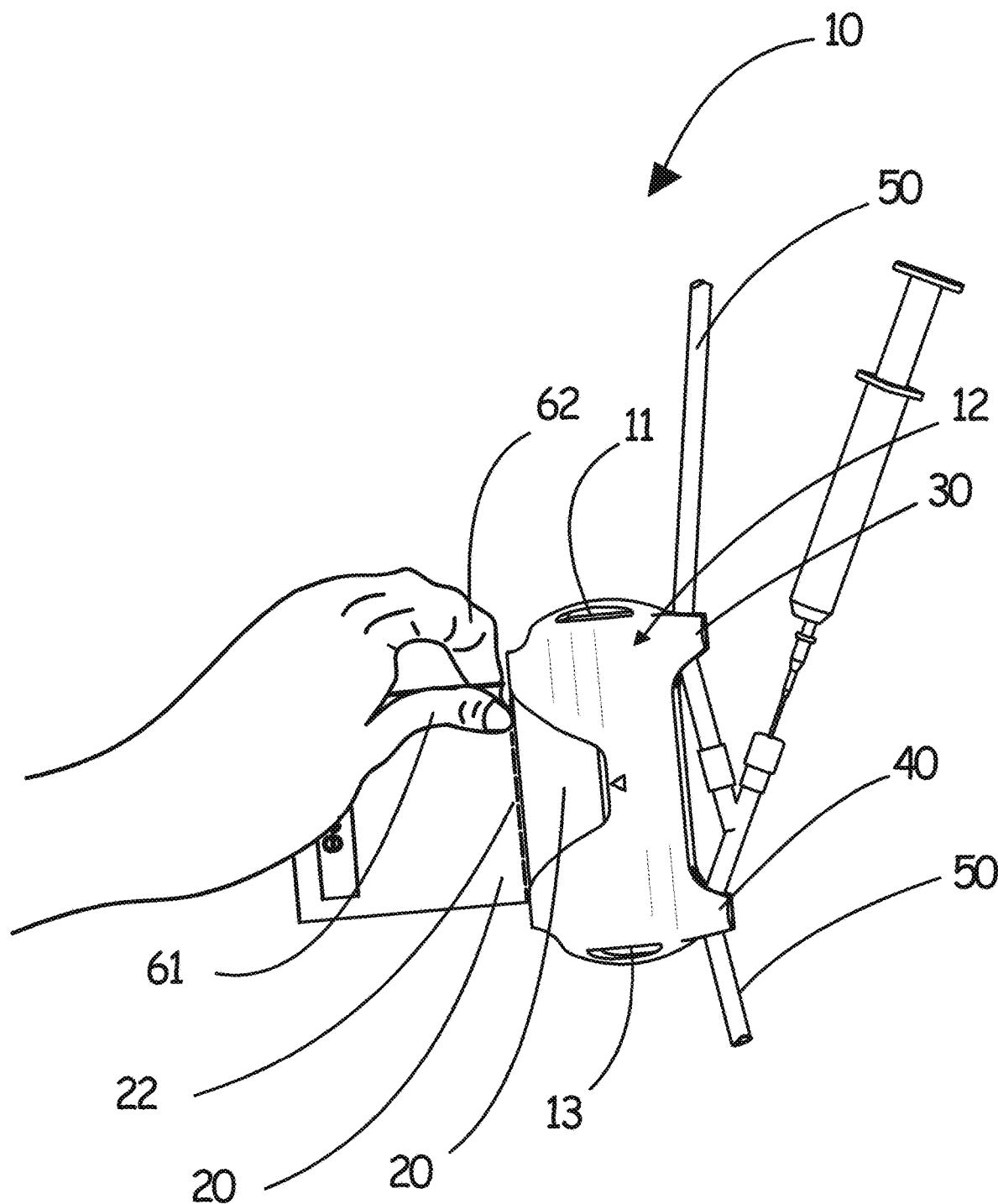
FIG. 11 is another environmental perspective view of dispenser apparatus of FIG. 1.

The attachment means can be comprised of a pair of outwardly extending attachment members 30, 40 positioned proximate opposite longitudinal ends of the housing 12, as shown in FIGS. 4 and 8. Each attachment member 30, 40 comprises an upper segment 31, 41, respectively, and a lower segment 32, 42, respectively. The upper segments 31, 41 and lower segments 32, 42 together define a curved cavity 33, 43, as shown in FIGS. 4, 5, 6 and 8. The curved cavities 33, 43 are sized and shaped to receive and frictionally engage the IV tubing line 50, as shown in FIGS. 10 and 11. As shown in FIGS. 5, 6 and 7A, each of the upper segments 31, 41 and lower segments 32, 42 have a concave surface 31a, 32a, 41a, 42a and a slanted surface 31b, 32b, 41b, 42b in communication with the concave surface 31a, 32a, 41a, 42a, respectively. The slanted surfaces 31b, 32b, 41b, 42b define a narrowing passageway wherein the distance between the upper segments 31, 41 and the lower segments 32, 42, respectively, is greatest at a position distal to the concave surfaces 31a, 32a, 41a, 42a and gradually decreases until the slanted surface 31a, 32a, 41a, 42a meet the concave surfaces 31a, 32a, 41a, 42a, as shown in FIGS. 5, 6, and 7A.

The housing 12 and the attachment members 30, 40 can be made of plastic or other suitable material. The attachment members 30, 40 can be integrally formed with the housing 12, to form a single unitary piece. The housing 12 and the attachment members 30, 40 can be made by injection molding, three-dimensional printing, or other suitable method. Alternatively, the attachment members 30, 40 can be separate pieces attached to the housing 12 by an adhesive, or other suitable attachment means.

The housing 12 contains a plurality of individually packaged, releasably attached applicator wipes 20. The applicator wipes 20 can be sterile sanitizing wipes comprised of paper, cloth, non-woven fibers and/or other suitable material that is soaked in a disinfecting solution, such as a solution of 60-99% isopropyl alcohol in water. Other disinfecting solutions include a solution of 70% ethanol in water, and 3% hydrogen peroxide in water. Each wipe 20 is packaged in its own packaging, and the individual packages are connected to each other in linear fashion and rolled up into a single roll 21, as shown in FIG. 9. The individual wipe 20 packages are connected by lines of perforation 22, as shown in FIG. 9.

Figure 7B:
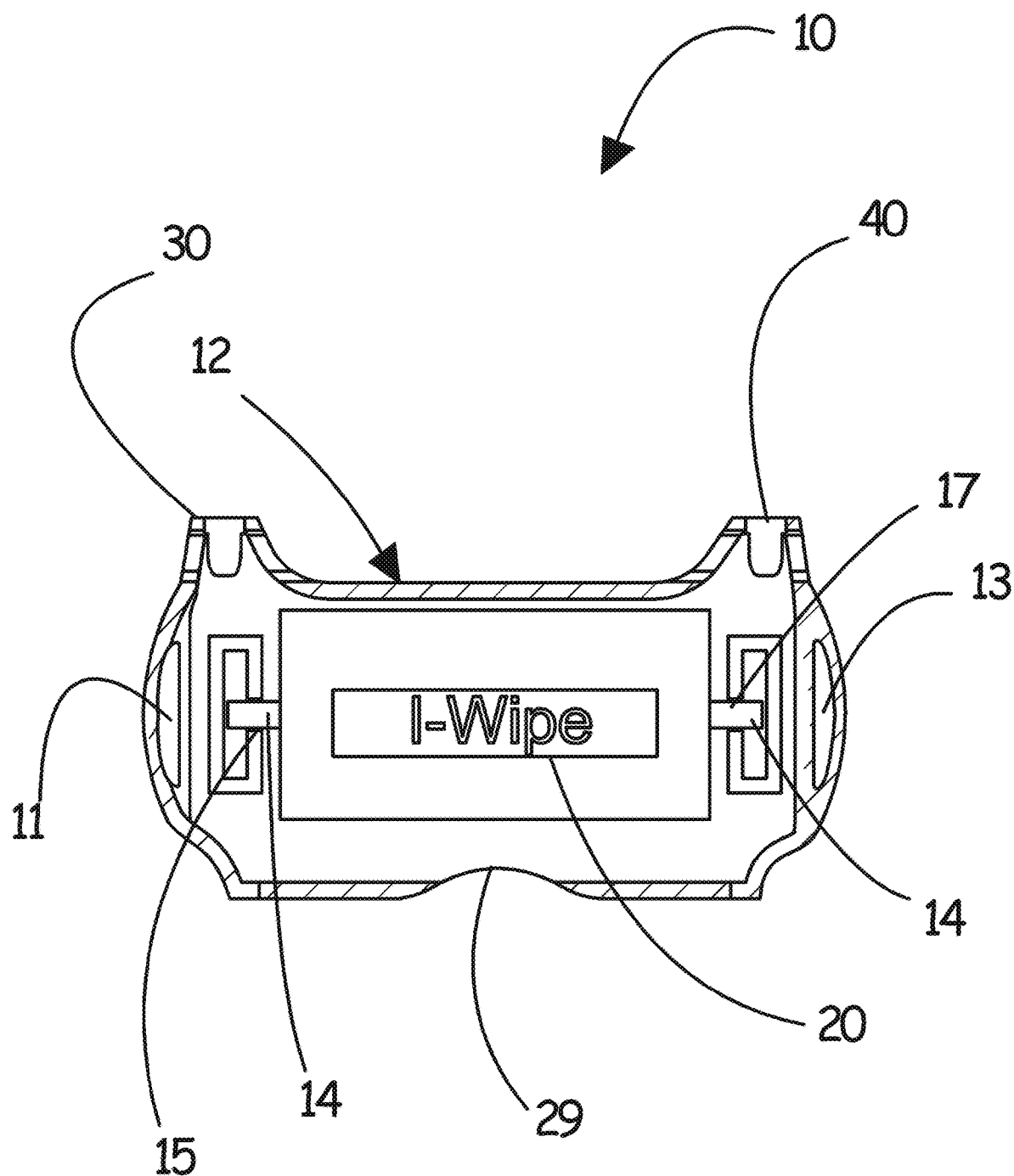
FIG. 7B is a cross sectional view of the dispenser apparatus of FIG. 1, taken along lines 7B-7B in FIG. 5.

The apparatus 10 can include a rolling mechanism that supports and facilitates rotation of the roll 21 of wipes 20. The rolling mechanism can comprise a rolling member, such as a rotatable rod 14, that is mounted in apertures 15, 17 formed at opposite ends of the interior of the housing, as shown in FIGS. 7A and 7B. The connected wipes 20 are rolled onto the rod 14 mounted inside the housing 12, as shown in FIG. 7B.

Figure 3:
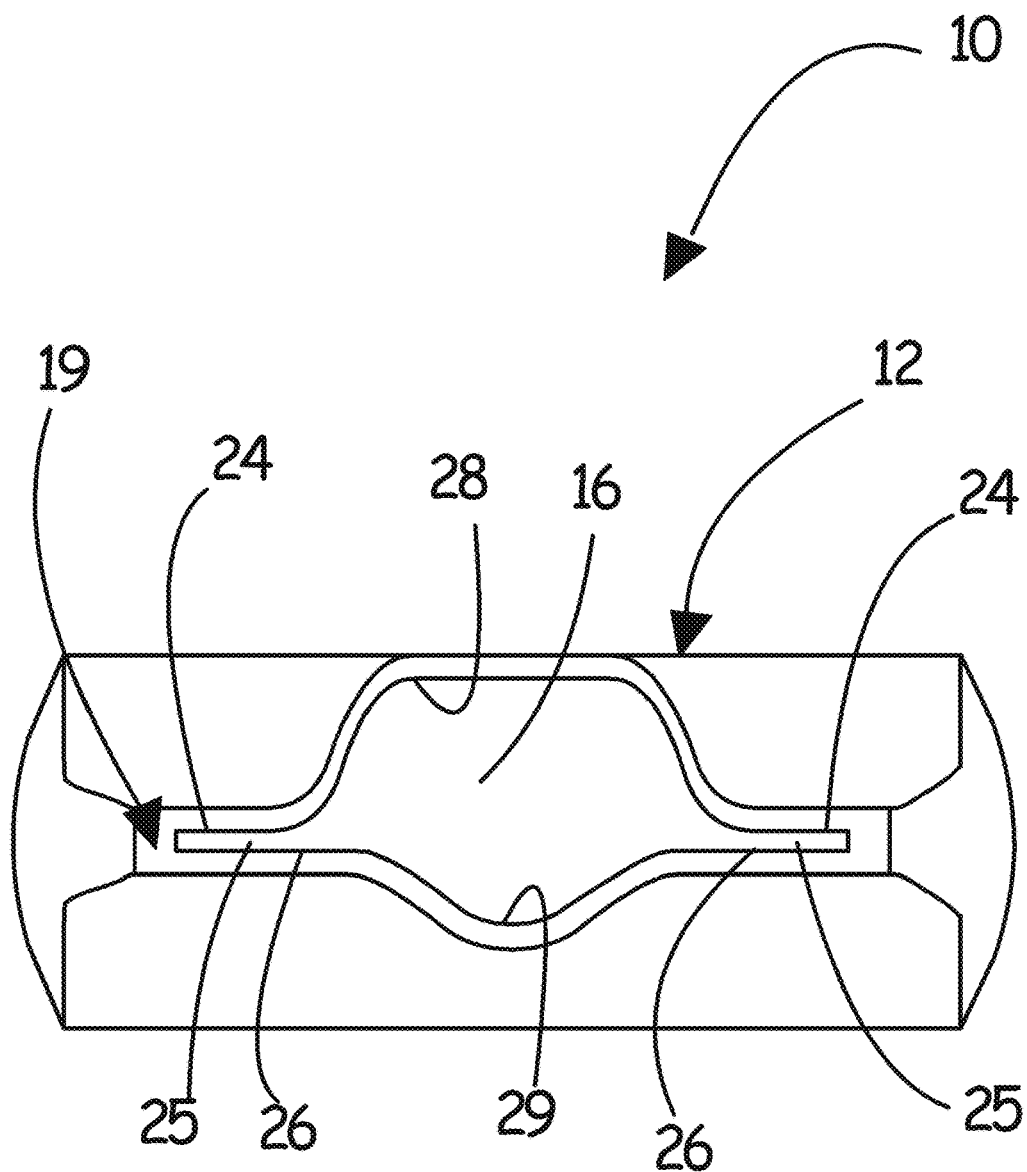
FIG. 3 is a front view of the dispenser apparatus of FIG. 1.

The housing 12 includes a dispensing opening 16, shown in FIG. 3, through which the wipes 20 can be pulled through. The dispensing opening 16 is defined by a dispensing lip section 19 formed on the housing 12 and extending outwardly therefrom, as shown in FIGS. 3 and 5. The dispensing opening 16 is located on the housing 12 about 180 degrees from the attachment members 30, 40, as shown in FIG. 5. The lip section 19 comprises first and second spaced apart edge sections 24, 26, as shown in FIGS. 3 and 6. The edge sections 24, 26 are substantially parallel to each other and define a slit 25 sized to receive one of the packaged applicator wipes there through, as shown in FIG. 10.

Figure 1:
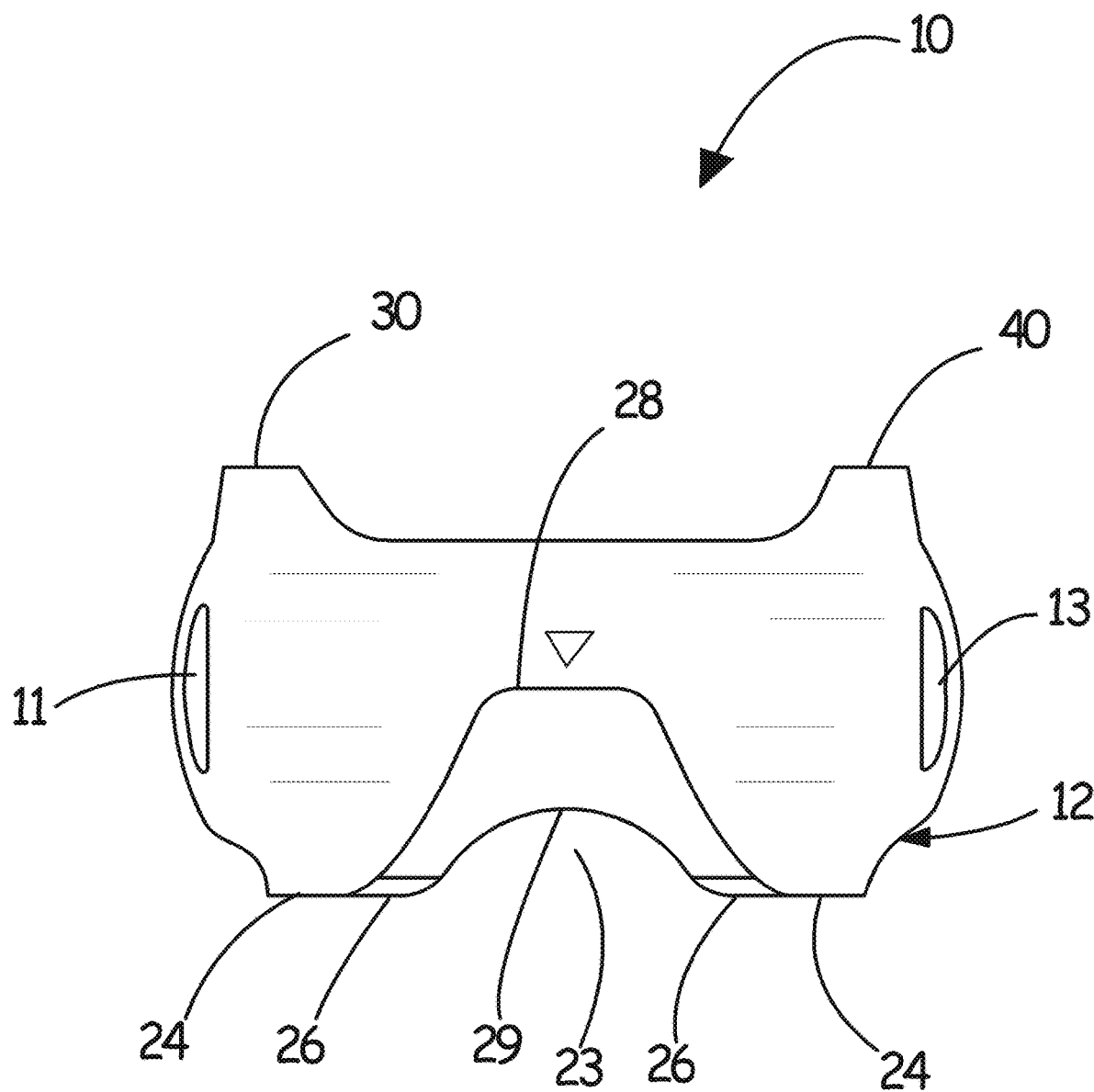
FIG. 1 is a top plan view of a dispenser apparatus according to an embodiment of the invention.
Figure 2:
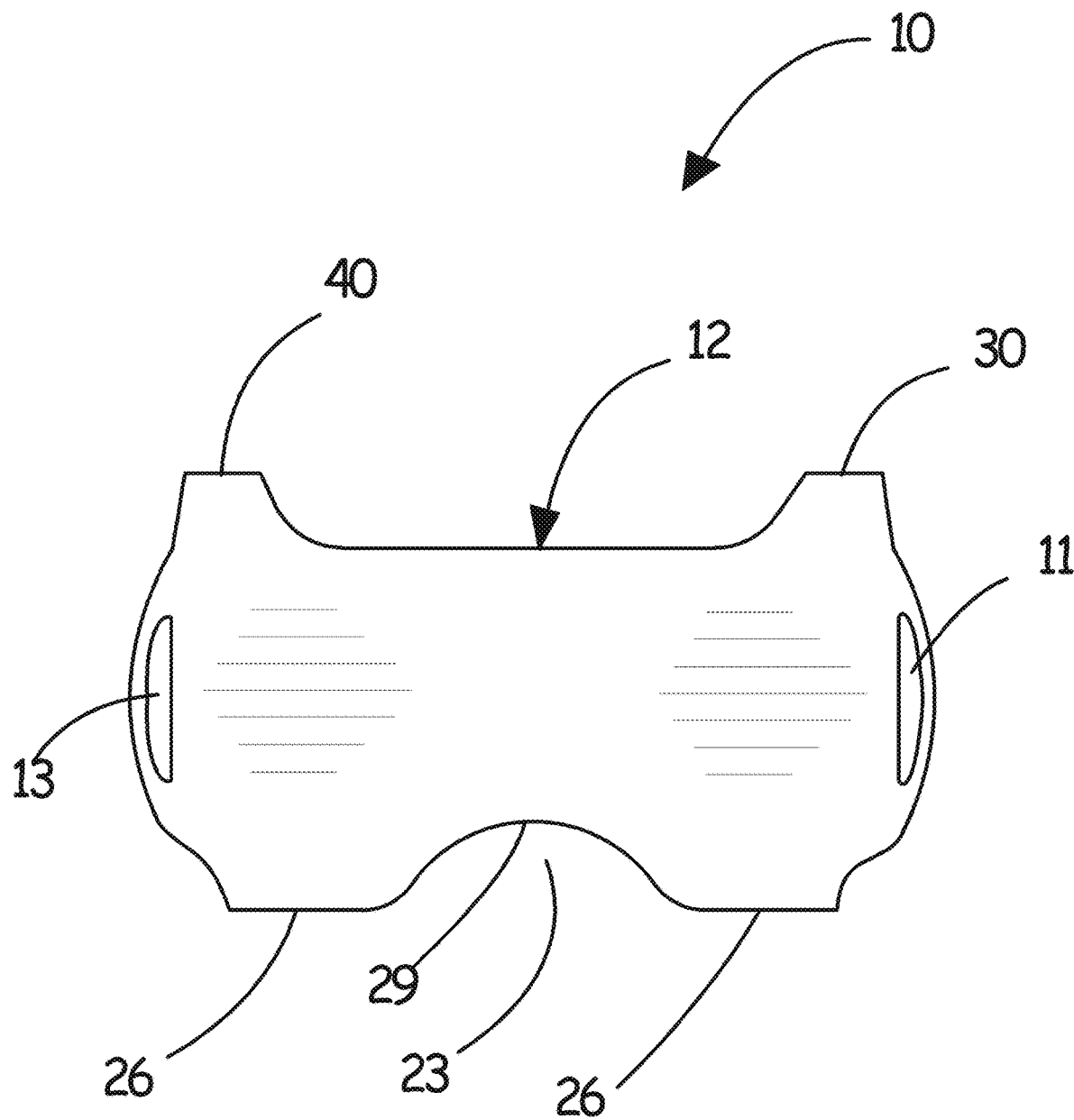
FIG. 2 is a bottom plan view of the dispenser apparatus of FIG. 1.

First and second cut away sections 28, 29 are formed in the housing 12. The first cut away section 28 is substantially "U" shaped and in communication with the first edge section 24, as shown in FIGS. 1, 3 and 6. The second cut away section 29 is substantially "U" shaped and in communication with the second edge section 26, as shown in FIGS. 2, 3 and 6. Preferably, the first cut away section 28 is substantially deeper than the second cut away section 29, as shown in FIGS. 1 and 3. The first cut away 28 section provides an exposed area 18 that exposes the first applicator wipe 20 of the roll 21 of applicator wipes 20 contained in the housing 12, as shown in FIGS. 1 and 8. The second cut away section 29 provides a smaller exposed area 23, as shown in FIGS. 1 and 2. The first exposed area 18 provides an opening where a user can place a finger, such as a thumb 61, onto the lead off applicator wipe 20, and the second exposed area 23 allows the user to place another finger, such as the index finger 62, onto the opposite side of the lead off wipe 20, and the user can pull the lead off wipe 20 out of the housing 12 through the slit 16.

Once a single wipe 20 has been pulled fully out of the housing 12, the user can tear it off from the rest of the wipes 20 remaining within the housing 12 along its line of perforation 22, as shown in FIGS. 10 and 11. The first and second edge sections 24, 26 provide stable surfaces against which the wipe 20 can be torn using only one hand, as shown in FIGS. 10 and 11. This results in a single wipe 20 that is detached from the remaining connected wipes 20, with its packaging opened and ready for use.

The housing 12 can hold multiple pre-packaged wipes 20 perforated together in a single line and rolled onto the rolling member 14 that dispenses upon a person physically pulling a wipe 20 from the housing 12 and breaking the perforated tabs manually. The apparatus 10 can be a disposable, one-time use unit that is discarded when all wipes 20 within the housing 12 have been used.

The housing 12 can include a pair of eyelets 11, 13 formed on the housing 12 at opposite longitudinal ends of the housing 12, as shown in FIGS. 1 and 2. The eyelets 11, 13 can be integrally formed with the housing 12 as a single unitary piece, such as by injection molding. Alternatively, the eyelets 11, 13 can be separate pieces attached to the housing 12 by an adhesive, or other suitable attachment means.

In a preferred embodiment of the invention, the dispenser apparatus 10 can be attached on the IV line 50 near the port site. The apparatus 10 should be attached on the IV line 50 at a position where the apparatus 10 does not impede extensive view of the flowing fluid in the IV line 50 and does not pinch the tubing thereby impeding flow of the IV line 50. The apparatus 10 should be positioned such that it is highly visible and conveniently located to the source of use (port area). The apparatus 10 should be attached at a position on the IV line, in which it can be easily added and removed from IV line 50.

The apparatus 10 can be used for every patient with an initial IV placement connected to an IV bag and tubing, and other applications as per the discretion of the healthcare professional. The dispenser apparatus 10 can be referred to and marketed as an "I-Wipe". The outside packaging of the pre-packaged wipes 20 can be labeled with "I-Wipe". Either portions or the entirety of the housing 12 and the packaging of the wipes 20 can have a distinctively bright color, such as red, to draw attention to the healthcare professional and remind him or her to stop, disinfect, inject. For patient advocacy purposes, there can also be other items with "I-Wipe" printed on them to reinforce the message to the healthcare providers of the importance of wiping ports and other sterilizing applications.

The dispenser apparatus 10 allows convenient access to alcohol wipes for the healthcare professional on IV tubing to reduce the risk of infection and increase productivity. The apparatus 10 supplies disinfecting wipes 20, and also provides a more convenient and hard stop reminder for healthcare professionals to think about the safe IV infusion practice of wiping the port for fifteen seconds prior to injecting a medication. The apparatus 10 can also be used for sterilization applications other than IV infusion.

Figure 12:
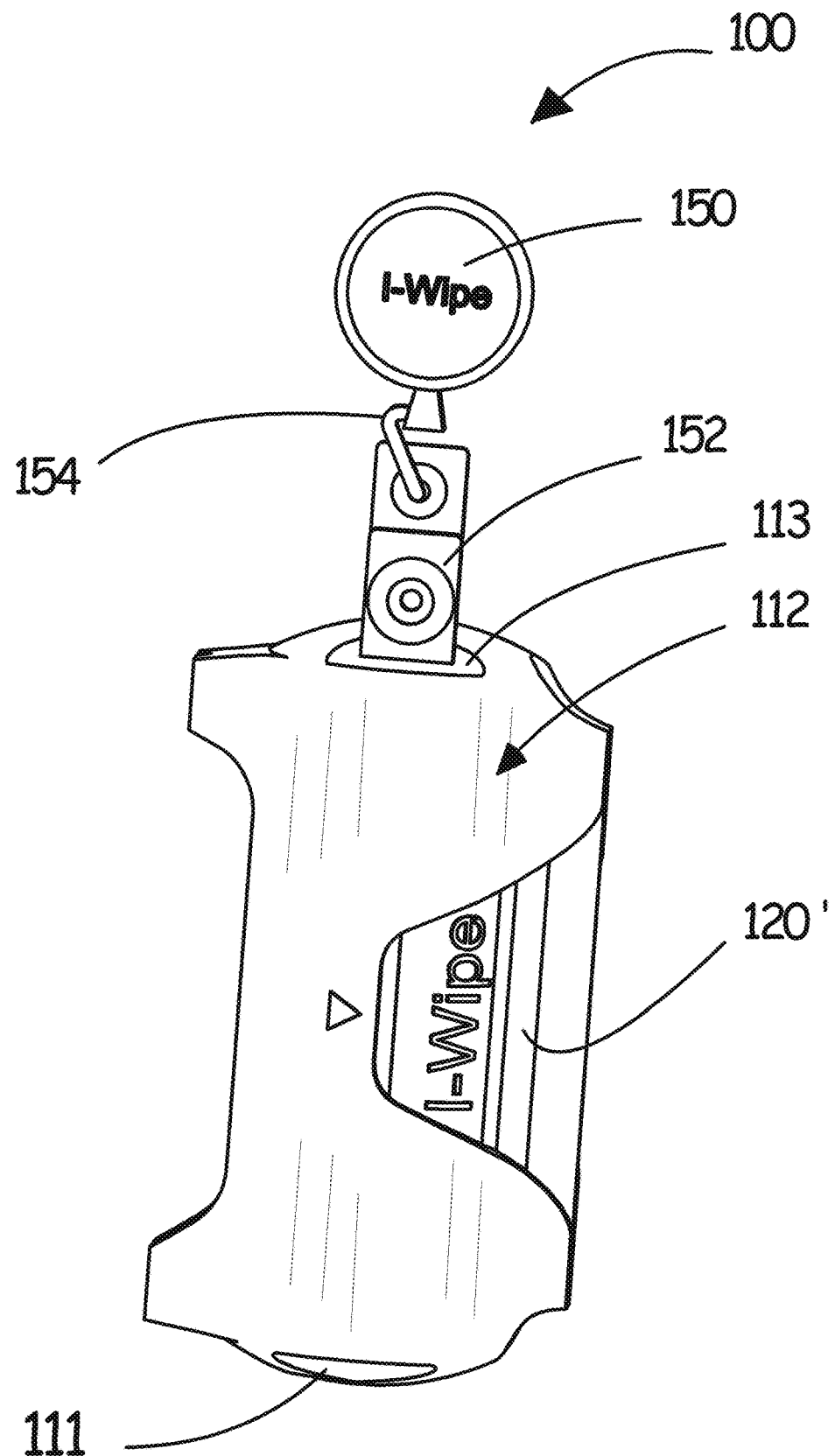
FIG. 12 is a perspective view of a dispenser apparatus according to another embodiment of the invention.
Figure 13:
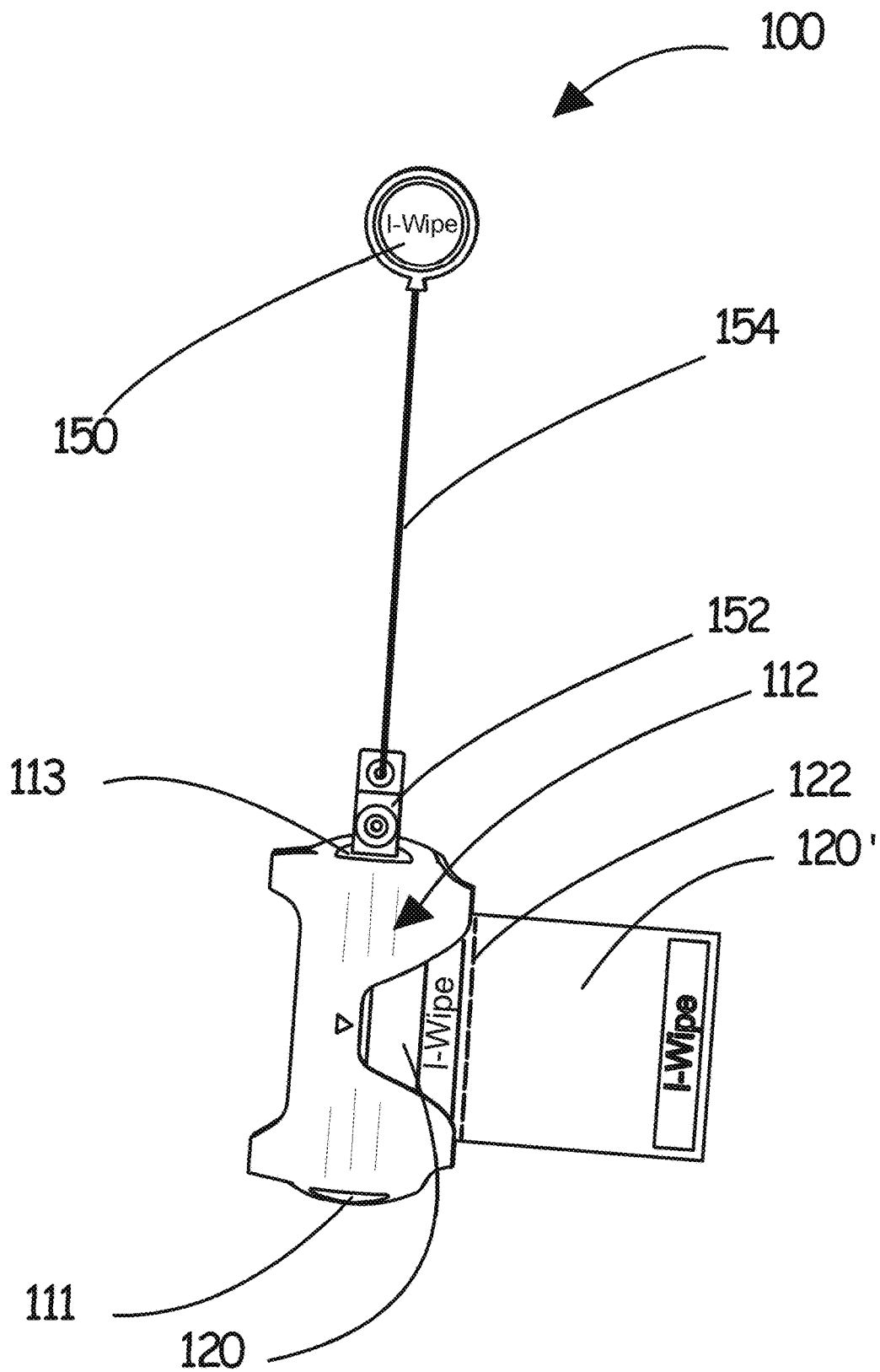
FIG. 13 is another perspective view of the dispenser apparatus of FIG. 12.

A dispenser apparatus according to another preferred embodiment of the invention is illustrated in FIGS. 12 and 13, and shown generally at reference numeral 100. The dispenser apparatus 100 comprises a generally cylindrical housing 112 identical in structure to the housing 12 of the previously described dispenser apparatus 10. In addition, the apparatus 100 includes a fastening member 150 that is connected to the housing 112, and is adapted for attaching to clothing or other support structure.

The housing 112 contains a plurality of packaged, releasably attached applicator wipes 120. Each wipe 120 is packaged in its own packaging, and the individual packages are connected to each other in linear fashion. The individual wipe 120 packages are connected by perforated lines. The connected packaged wipes 120 are rolled onto a cylindrical rolling member positioned inside the housing 112. As shown in FIG. 13, the first wipe 120' on the roll can be pulled through the dispensing opening 116 and torn along the perforation 122, which connects the first wipe 120' to a second wipe 120 still contained within the housing 112.

The fastening member 150 contains a retractable cord 154, as shown in FIGS. 12 and 13. An end of the retractable cord 154 can be attached to a snap fastener 152 that is received through the either one of the eyelets 111, 113 on the housing 112 of the dispenser 100, thereby connecting the housing 112 to the fastening member 150.

The fastening member 150 includes attachment means for releasably attaching the fastening member 150 onto the clothing of a user. The attachment means can be an adhesive, a spring-loaded clip, a pin, one or more magnets, or other suitable fasteners. The fastening member 150 can also be attached to items other than clothing.

The retractable cord 154 is housed within the body of the fastening member 150, and the exposed end of the retractable cord 154 is attached to the snap fastener 152, as shown in FIGS. 12 and 13. The retractable cord 154 can be pulled out of the fastening member 150, as shown in FIG. 13. This allows for freedom of movement of the apparatus 100, while still remaining connected to the clothing of the user. For example, the attachment member 150 can be attached to the chest area of the user, and when the user needs a wipe 120, the user can grasp the dispenser housing 112, and pull the housing 112 to a position that is comfortable for removing a wipe 120.

When all wipes 120 in the dispenser housing 112 have been used, the housing 112 can be detached from the snap fastener 152 and discarded. A new dispenser housing 112 with a fresh supply of wipes 120 can then be attached to the snap fastener 152. As such, the dispenser housing 112 can be disposable, while the attachment member 150 is reusable.

Figure 14:
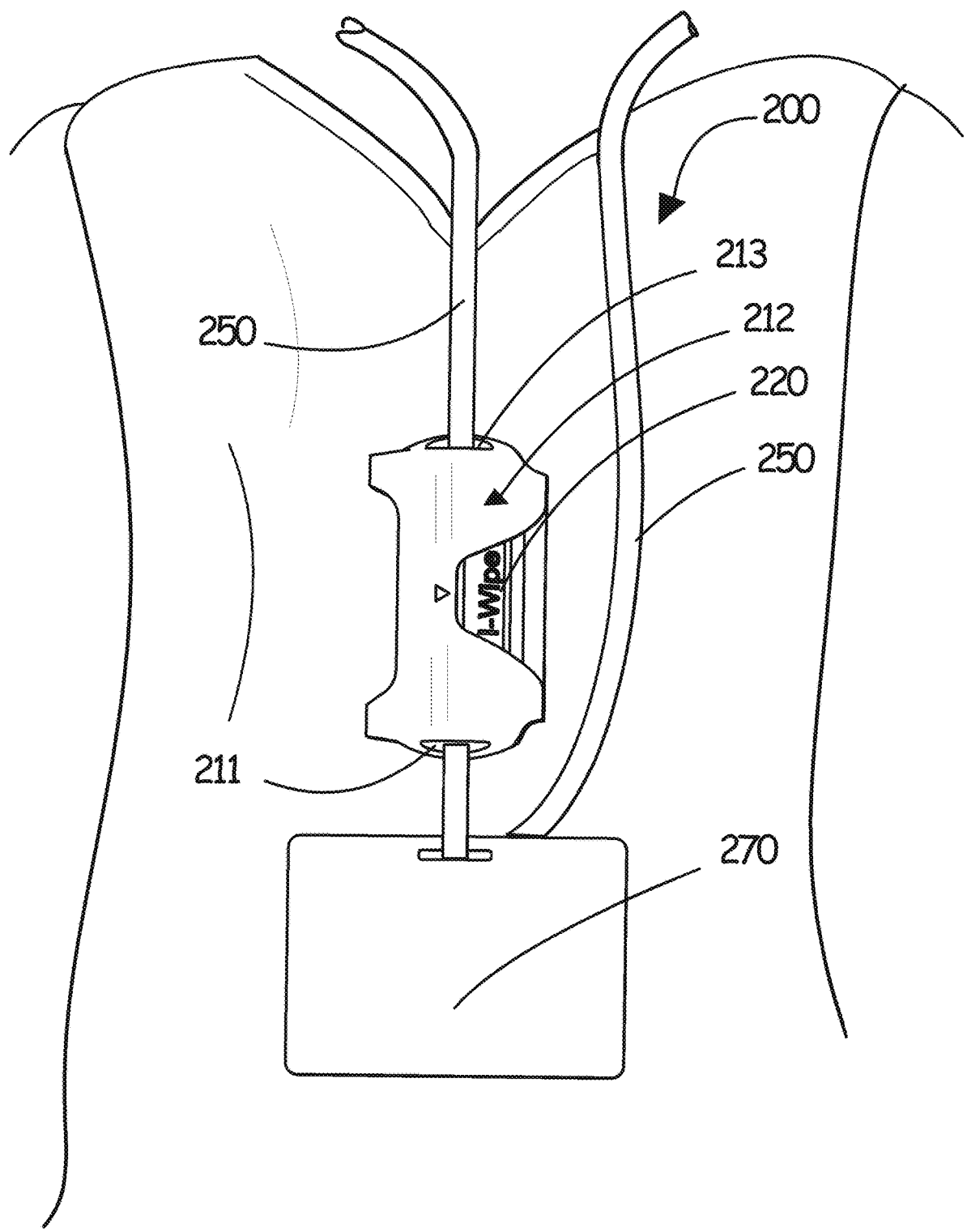
FIG. 14 is another environmental perspective view of the dispenser apparatus of FIG. 1.
Figure 15:
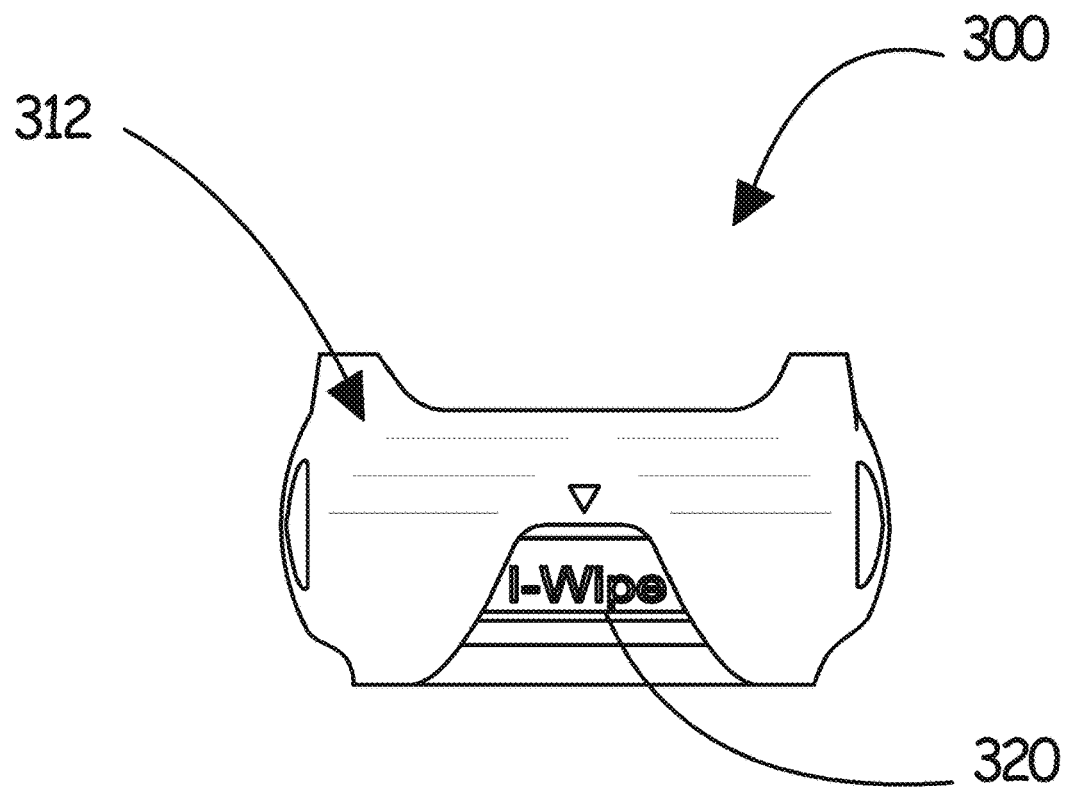
FIG. 15 is a top plan view of a dispenser apparatus according to another embodiment of the invention.
Figure 16:
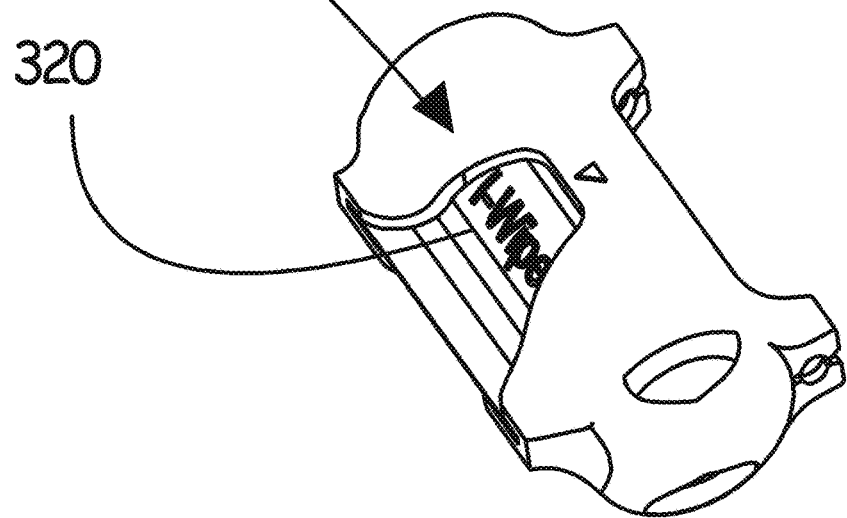
FIG. 16 is a perspective view of the dispenser apparatus of FIG. 15.

A dispenser apparatus according to another preferred embodiment of the invention is illustrated in FIG. 14, and shown generally at reference numeral 200. The dispenser apparatus 200 comprises a dispenser housing 212 attached to a lanyard 250.

The housing 212 is identical in structure to housing 12 of the previously descripted dispenser apparatus 10. The housing 212 contains applicator wipes 220 perforated together in a single line and rolled onto a rolling member that dispenses upon a person physically pulling a wipe 220 from the housing 212 and breaking the perforated tabs manually.

The dispenser housing 212 is attached to the lanyard 250 by running the lanyard 250 through the eyelets 211, 213 formed on the housing 212, as shown in FIG. 14. Alternatively, the lanyard 250 can include a fastener, such as an alligator clamp, that engages one of the eyelets 211, 213 of the housing. The lanyard 250 can be worn around the neck of a healthcare professional. The lanyard 250 can also be used to carry other items, such as a hospital identification tag 270. The dispenser housing 212 can be disposable. As such, when all wipes 220 have been used, the dispenser housing 212 can be removed from the lanyard 250 and replaced with a new housing having a fresh supply of wipes 220.

Figure 17:
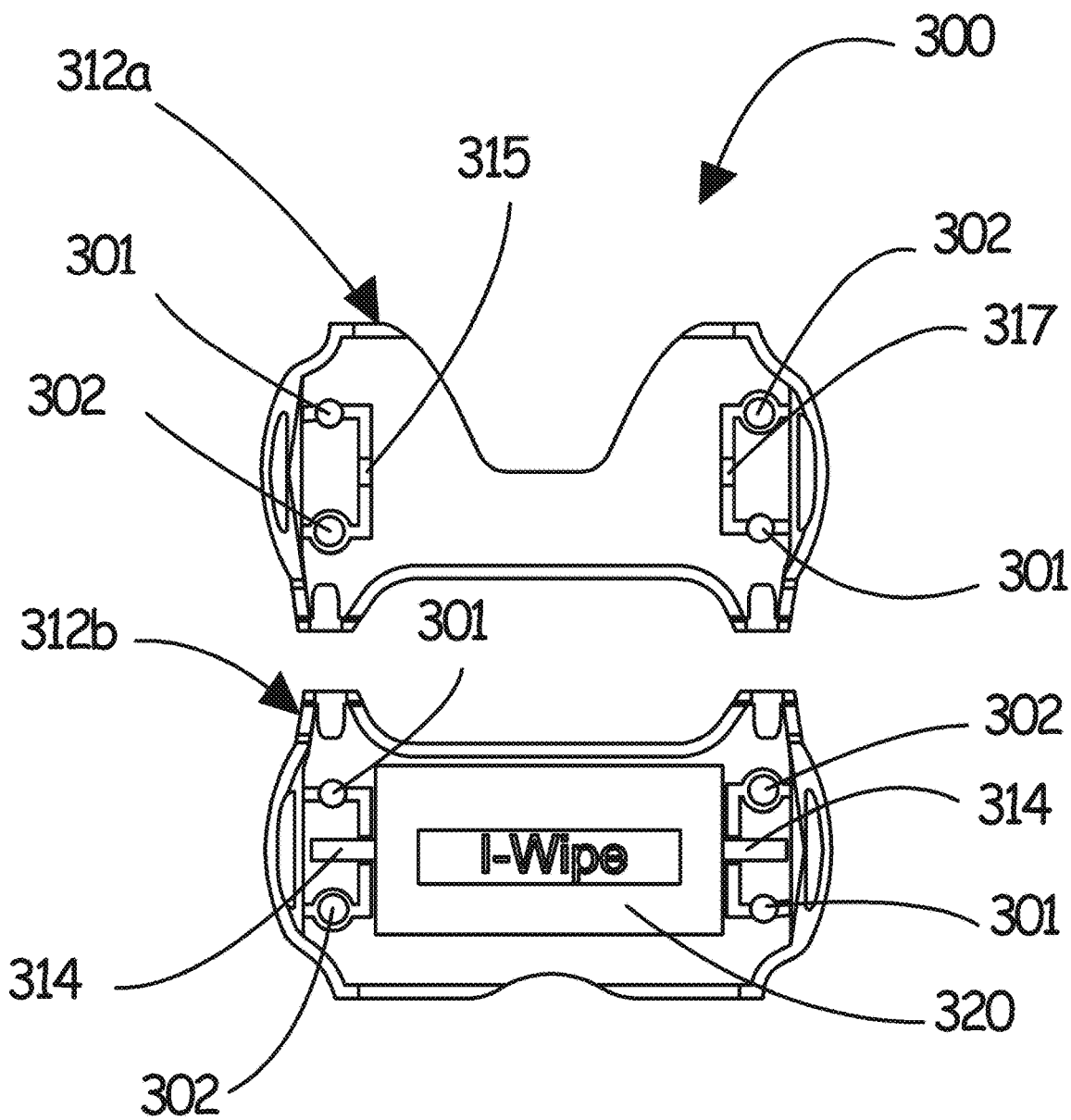
FIG. 17 is an exploded view of the dispenser apparatus of FIG. 15.
Figure 18:
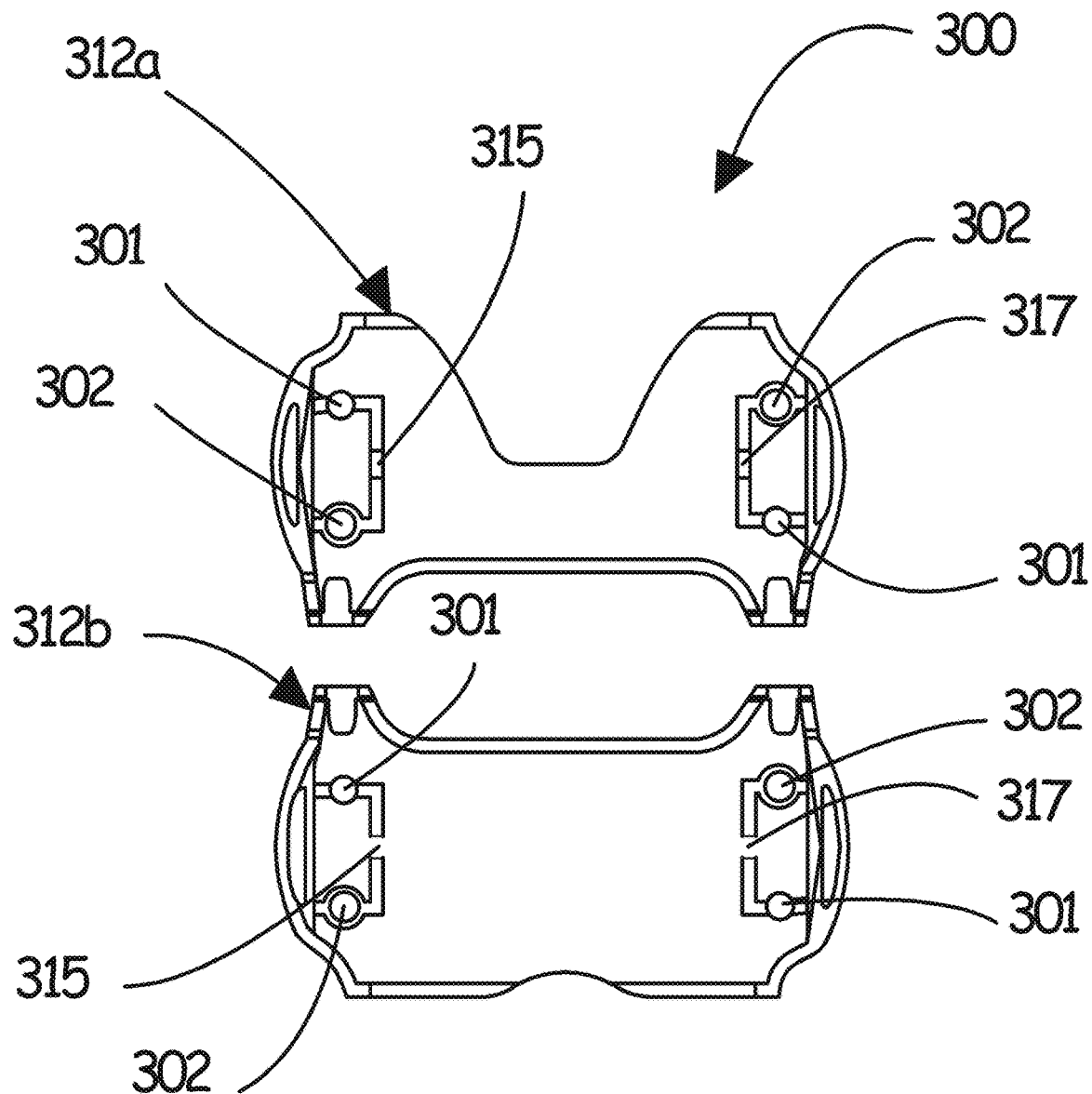
FIG. 18 is another exploded view of the dispenser apparatus of FIG. 15.

A dispenser apparatus according to another preferred embodiment of the invention is illustrated in FIGS. 15-18 and shown generally at reference numeral 300. The dispenser apparatus 300 is identical in structure to the previously described apparatus 10, except that dispenser apparatus 300 comprises a housing 312 that is comprised of a pair of releasably attached body sections 312a, 312b having complementary fasteners 301, 302, as shown in FIGS. 17 and 18.

Each housing body section 312a, 312b includes complementary fasteners adapted for releasable engagement to each other. As shown in FIGS. 17 and 18, the body sections 312a, 312b have outwardly extending pins 301 and complementary apertures 302 positioned within the interior of the body sections 312a, 312b such that the pins 301 are received and frictionally engaged in the apertures 302 when one body section 312a is properly positioned on the other body section 312b. As such, when all applicator wipes 320 have been removed from the apparatus 300 the housing 312 can be opened by pulling apart body sections 312a, 312b, and a new roll of applicator wipes can be positioned therein.

The apparatus 300 can include a rolling mechanism comprising a rotatable rod 314 mounted in apertures 315, 317 formed at opposite ends of the interior of the housing, as shown in FIG. 17, which supports and facilitates rotation of the roll of applicator wipes 320. When a roll of wipes 320 has been exhausted, the housing body sections 312a, 312b can be separated and the rod 314 removed from the housing 312. A new roll of wipes is positioned on the rod 314, which is placed back onto the apertures 315, 317, and the housing body sections 312a, 312b are joined together again by the engagement of the complementary fasteners 301, 302.

Figure 19:
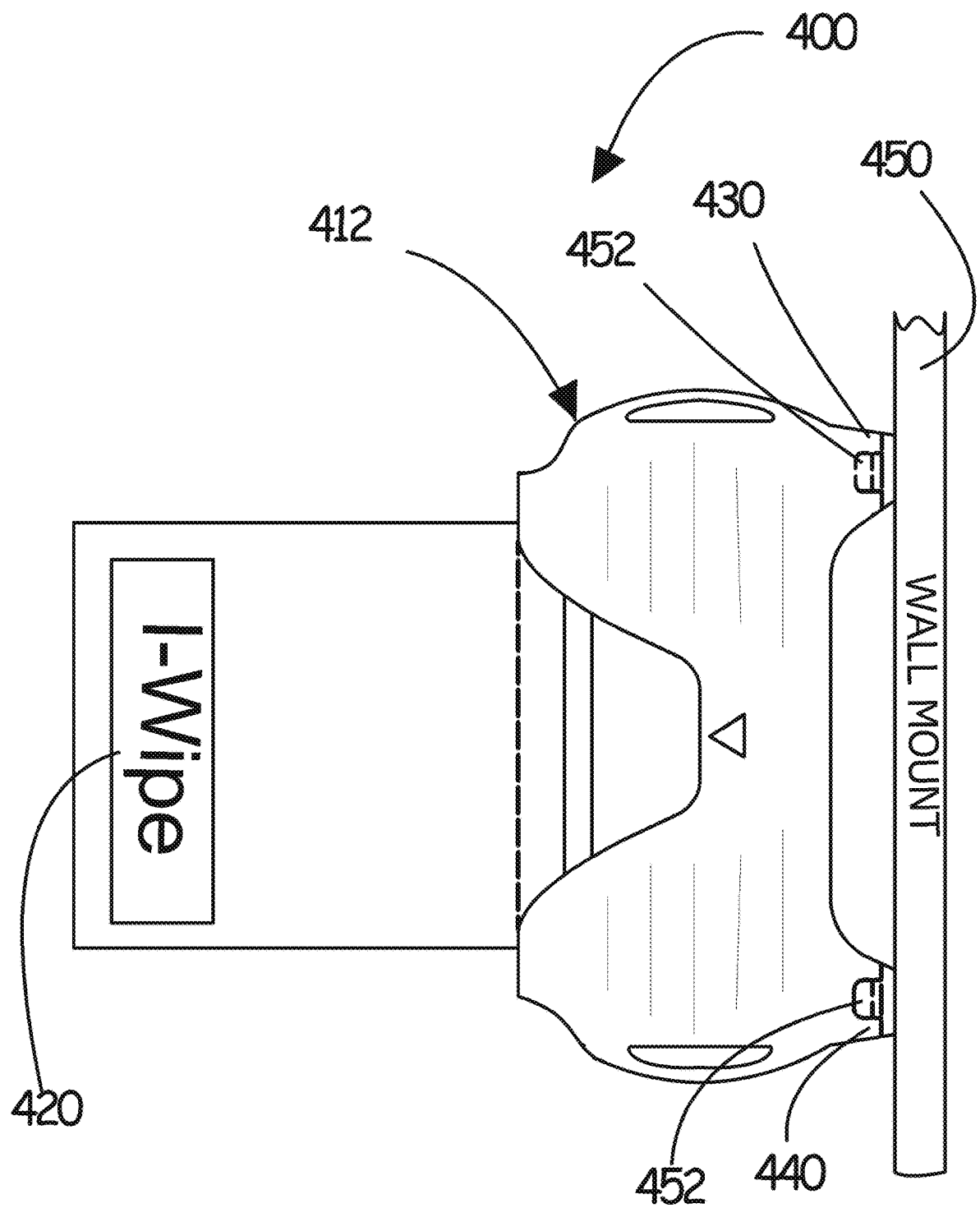
FIG. 19 is an environmental perspective view of a dispenser apparatus according to another embodiment of the invention.

A dispenser apparatus according to another preferred embodiment of the invention is illustrated in FIG. 19 and shown generally at reference numeral 400. The dispenser apparatus 400 is adapted for attachment to a wall 450, as shown in FIG. 19. The dispenser apparatus 400 comprises a housing 412 that is structurally similar to the previously described housing 12, except that the housing 412 includes attachment members 430, 440 that are adapted to engage fasteners 452 mounted on a wall. As shown in FIG. 19, knobs 452 can be mounted on the wall, and each of the attachment members 430, 440 can include a cavity shaped and sized for receiving the knobs 452. As such, the attachment members 430, 440 are slid onto the knobs 452 protruding outwardly from the wall 450, thereby attaching the dispenser apparatus 400 to the wall 450. The dispenser apparatus 400 dispenses a plurality of applicator wipes 420.

Figure 20:
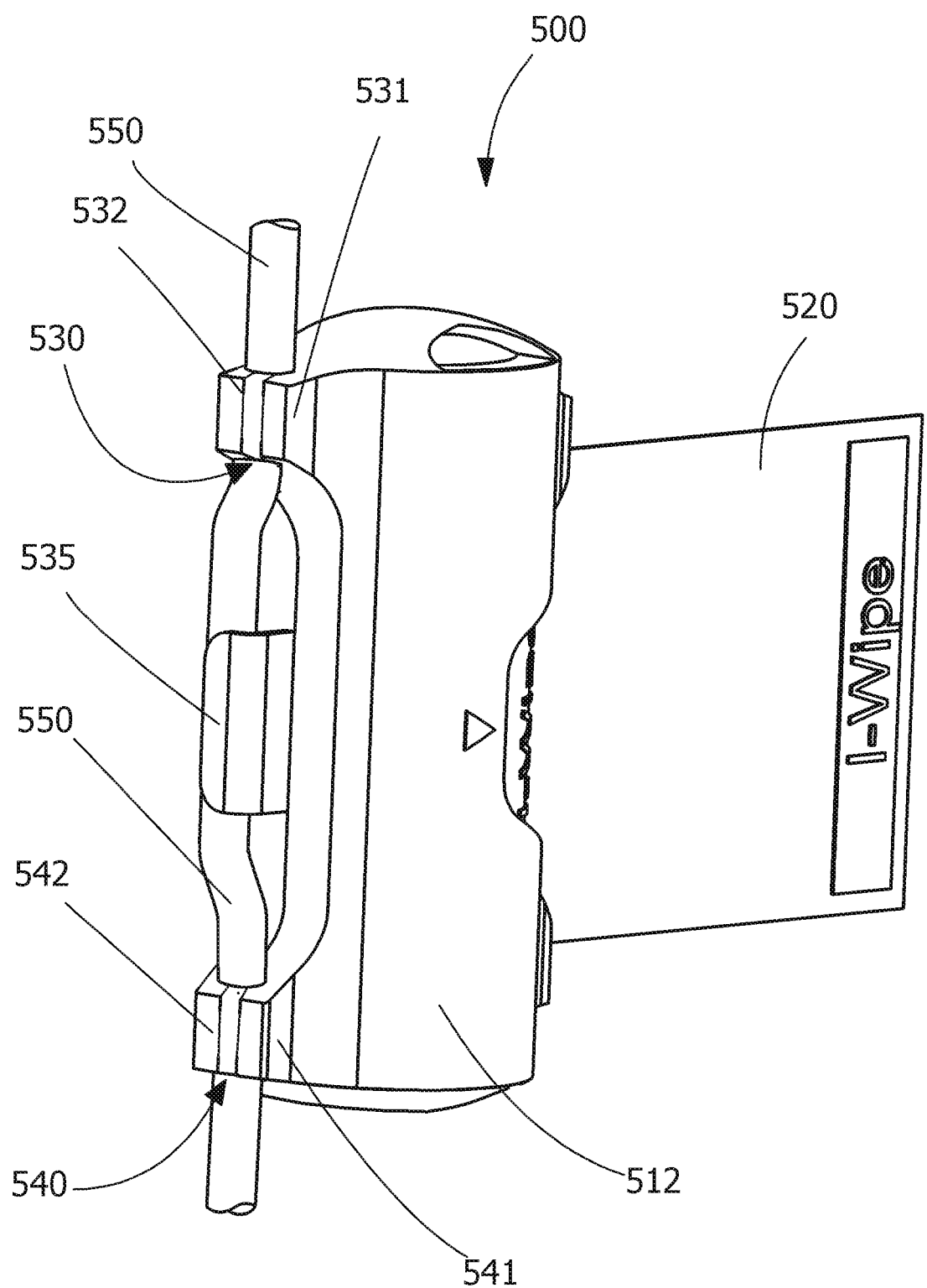
FIG. 20 is an environmental perspective view of a dispenser apparatus according to another embodiment of the invention.
Figure 21:
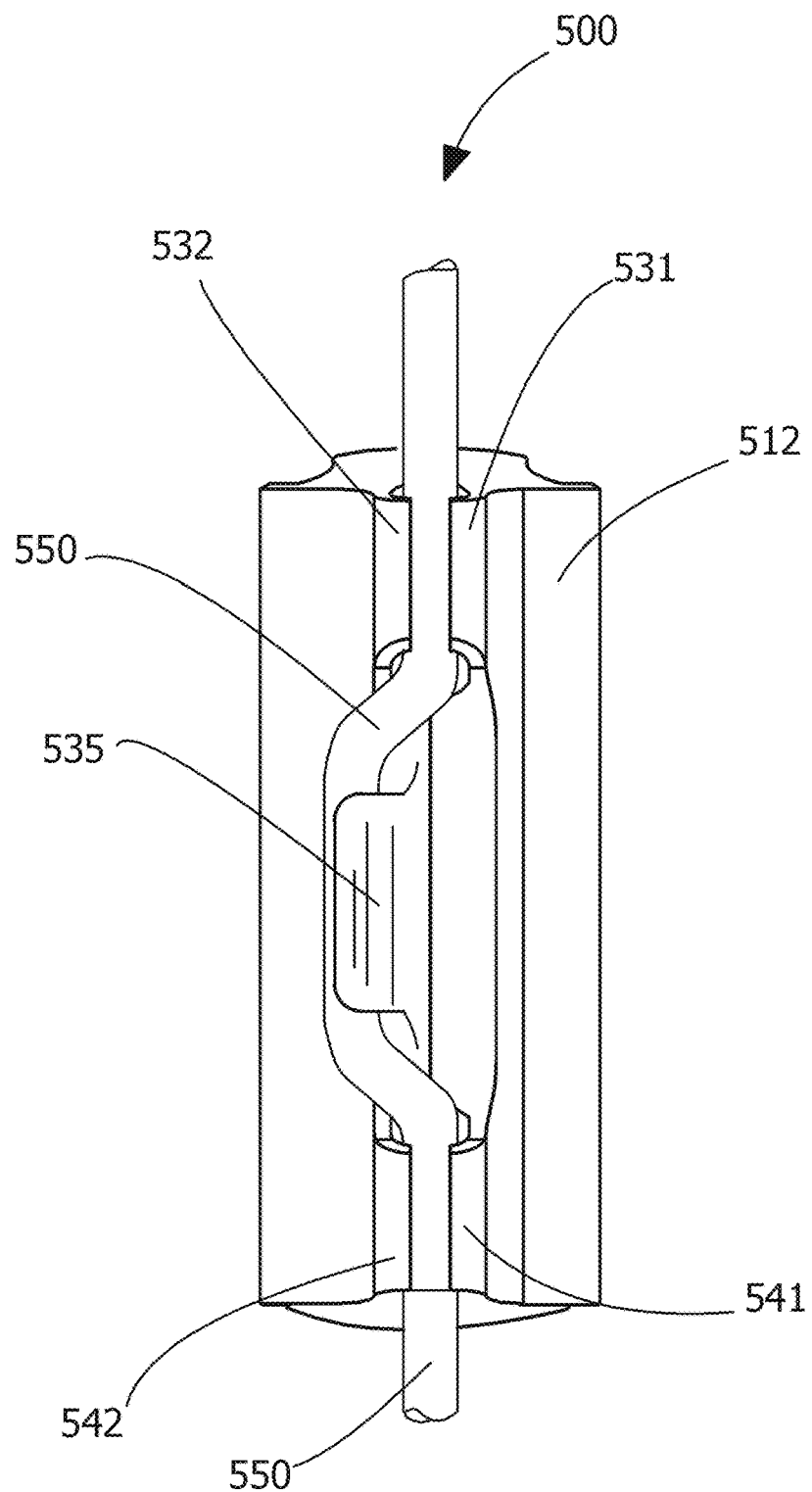
FIG. 21 is another environmental perspective view of the dispenser apparatus of FIG. 20.

A dispenser apparatus according to another preferred embodiment of the invention is illustrated in FIGS. 20-27, and shown generally at reference numeral 500. The apparatus 500 comprises a substantially cylindrical housing 512, and a pair of outwardly extending attachment members 530, 540 extending outwardly from the housing for attaching the housing 512 to an intravenous (IV) tubing line 550, as shown in FIGS. 20 and 21.

The housing 512 is adapted for containing a plurality of planar, interconnected items that are rolled up into a single roll. The interconnected items can be a plurality of individually packaged items, such as applicator wipes, in which each individual package is attached to another individual package along a line of perforation.

The attachment members 530, 540 are positioned proximate opposite longitudinal ends of the housing 512, as shown in FIGS. 20 and 21. The attachment members 530, 540 are linearly aligned on the housing 512, as shown in FIGS. 20 and 21. Each attachment member 530, 540 comprises a first segment 531, 541, respectively, and a complementary second segment 532, 542, respectively. The first segments 531, 541 and second segments 532, 542 together define arcuate cavities that are sized and shaped to receive and frictionally engage the IV tubing line 550, as shown in FIGS. 20, 21 and 23.

Figure 23:
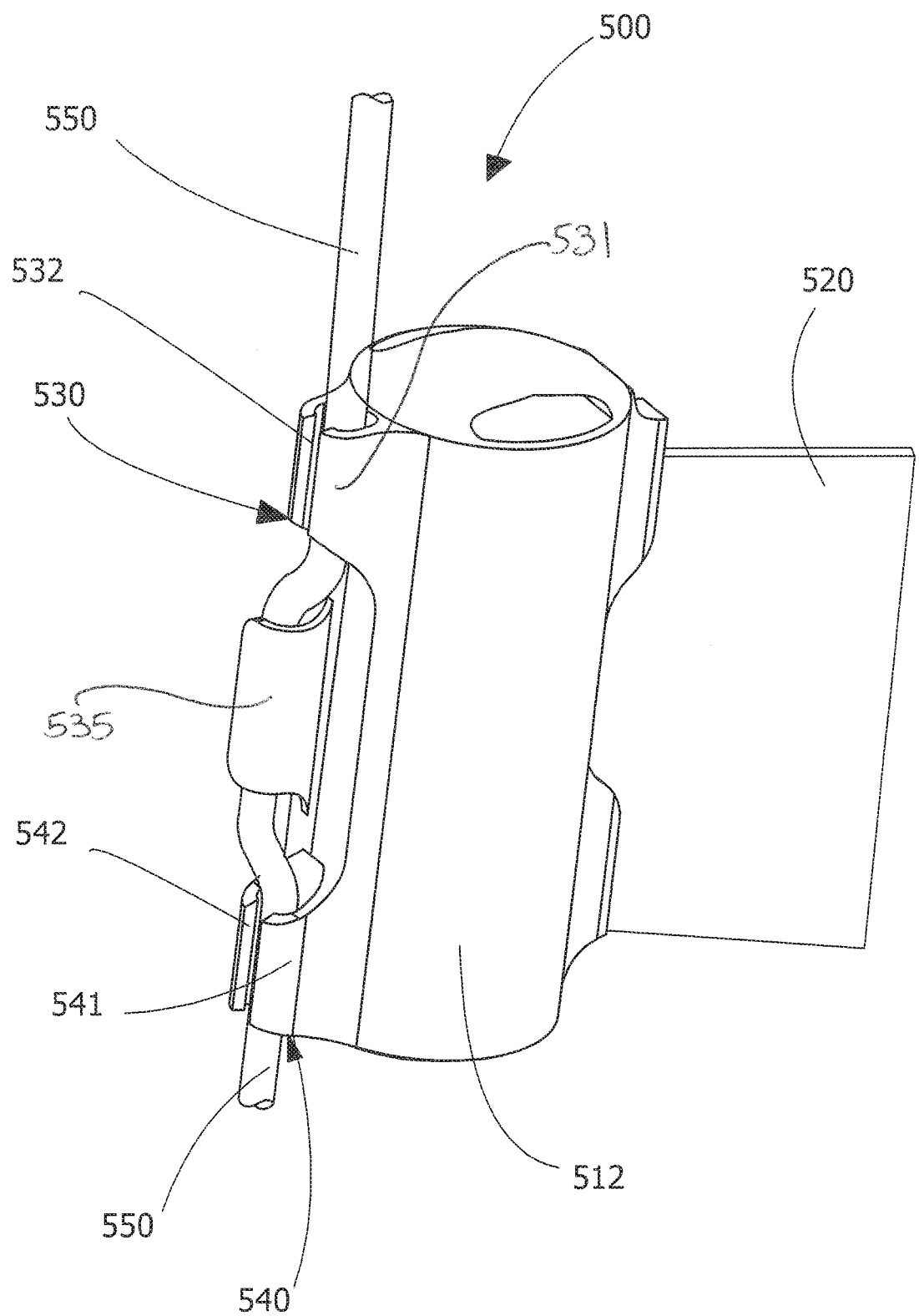
FIG. 23 is another environmental perspective view of the dispenser apparatus of FIG. 20.

A curved member 535 is positioned between the attachment members 530, 540, and extends outwardly from the housing 512, as shown in FIGS. 20, 21 and 23. The curved member 535 is preferably equidistance from each attachment member 530, 540. The curved member 535 has an arcuate curvature that substantially conforms to the cylindrical shape of the IV tubing line 550, as shown in FIGS. 20, 21 and 23. The curved member 535 contacts the tubing line and moves the tubing line 550, creating a slight angle in the tubing line 550 relative to the linearly aligned attachment members 530, 540, as shown in FIGS. 21 and 23. This improves the stability of the attachment members 530, 540 attached to the tubing line 550, without impeding the flow of fluid through the tubing line 550.

The housing 512, the attachment members 530, 540 and the curved member 535 can be made of plastic or other suitable material. The attachment members 530, 540 and the curved member 535 can be integrally formed with the housing 512, to form a single unitary piece. The housing 512, attachment members 530, 540 and curved member 535 can be made by injection molding, three-dimensional printing, or other suitable method. Alternatively, the attachment members 530, 540 and curved member 535 can be separate pieces attached to the housing 512 by an adhesive, or other suitable attachment means.

The housing 512 contains a plurality of individually packaged, releasably attached applicator wipes 520. The applicator wipes 520 can be sterile sanitizing wipes comprised of paper, cloth, non-woven fibers and/or other suitable material that is soaked in a disinfecting solution, such as a solution of 60-99% isopropyl alcohol in water. Other disinfecting solutions include a solution of 70% ethanol in water, and 3% hydrogen peroxide in water. Each wipe 520 can be packaged in its own packaging, and the individual packages are connected to each other in linear fashion and rolled up into a single roll 521. The plurality of individual wipe packages can be connected to each other by lines of perforation.

The apparatus 500 can include a rolling mechanism that supports and facilitates rotation of the roll 521 of wipes 520. The rolling mechanism can be a rolling member, such as a rotatable rod 514, that is mounted in apertures 515, 517 formed at opposite ends of the interior of the 512 housing, as shown in FIG. 23. The connected wipes 520 are rolled onto the rod 514 mounted inside the housing 512.

Figure 22:
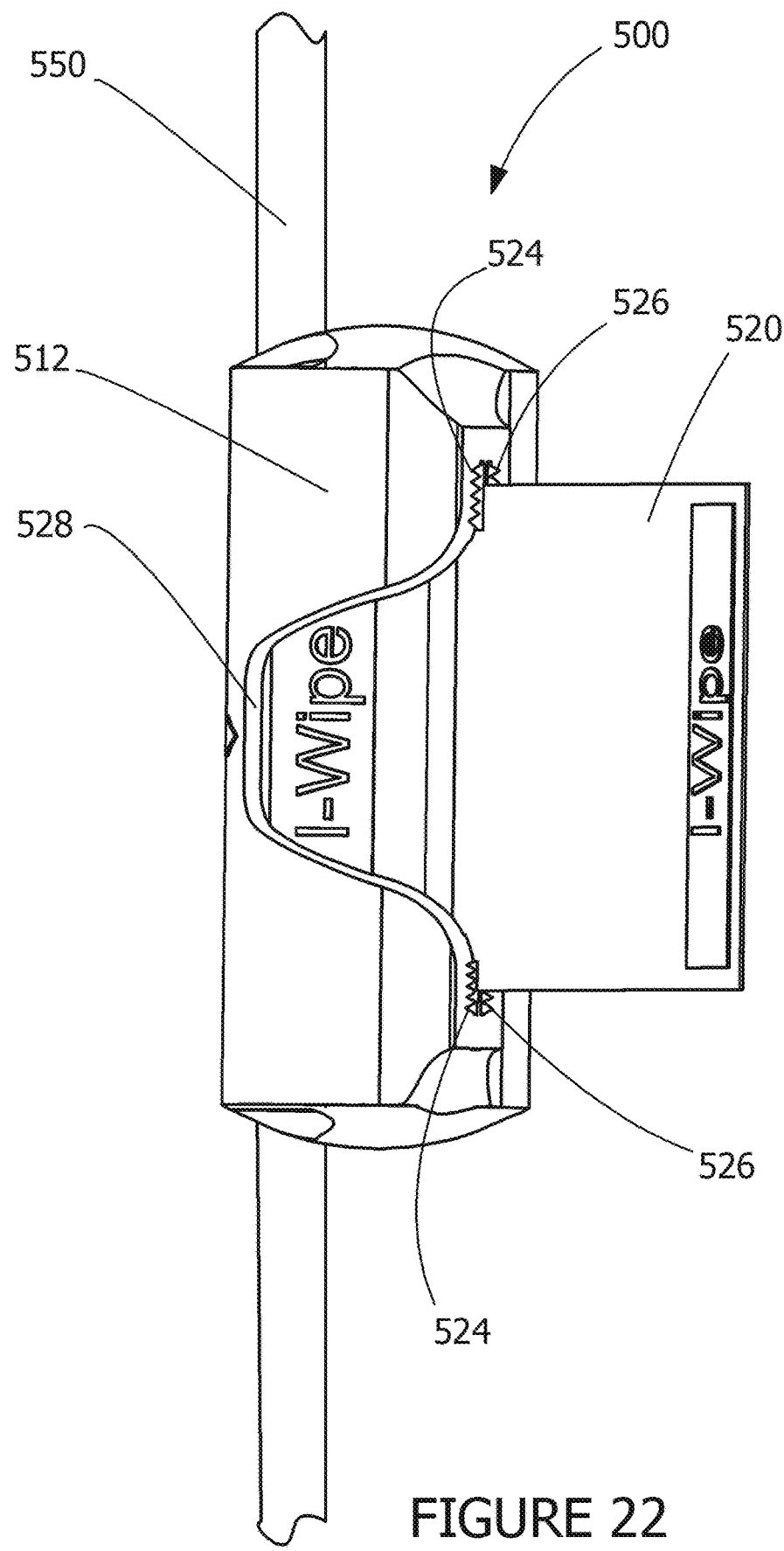
FIG. 22 is another environmental perspective view of the dispenser apparatus of FIG. 20.
Figure 24:
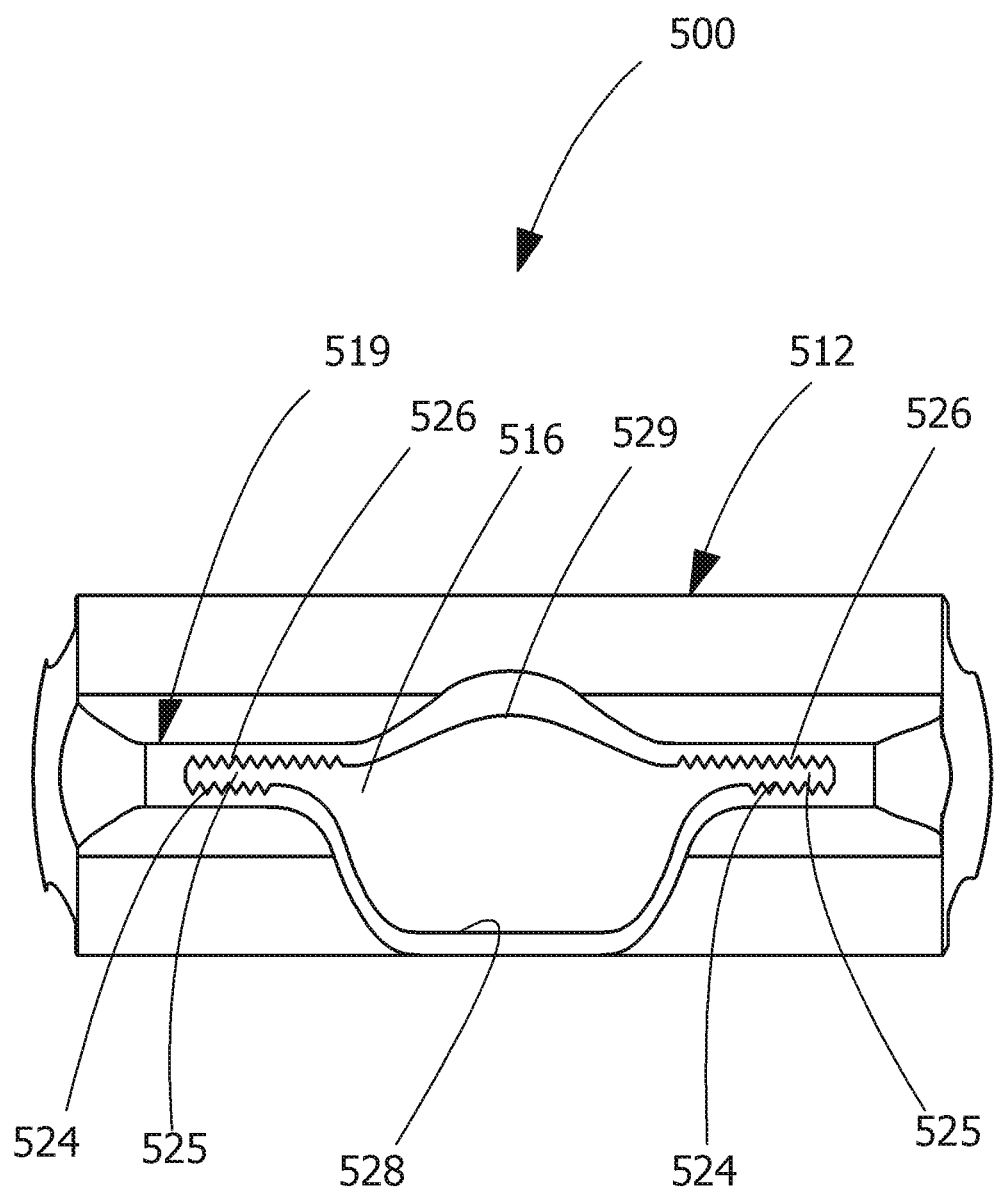
FIG. 24 is a front view of the dispenser apparatus of FIG. 20.
Figure 25:
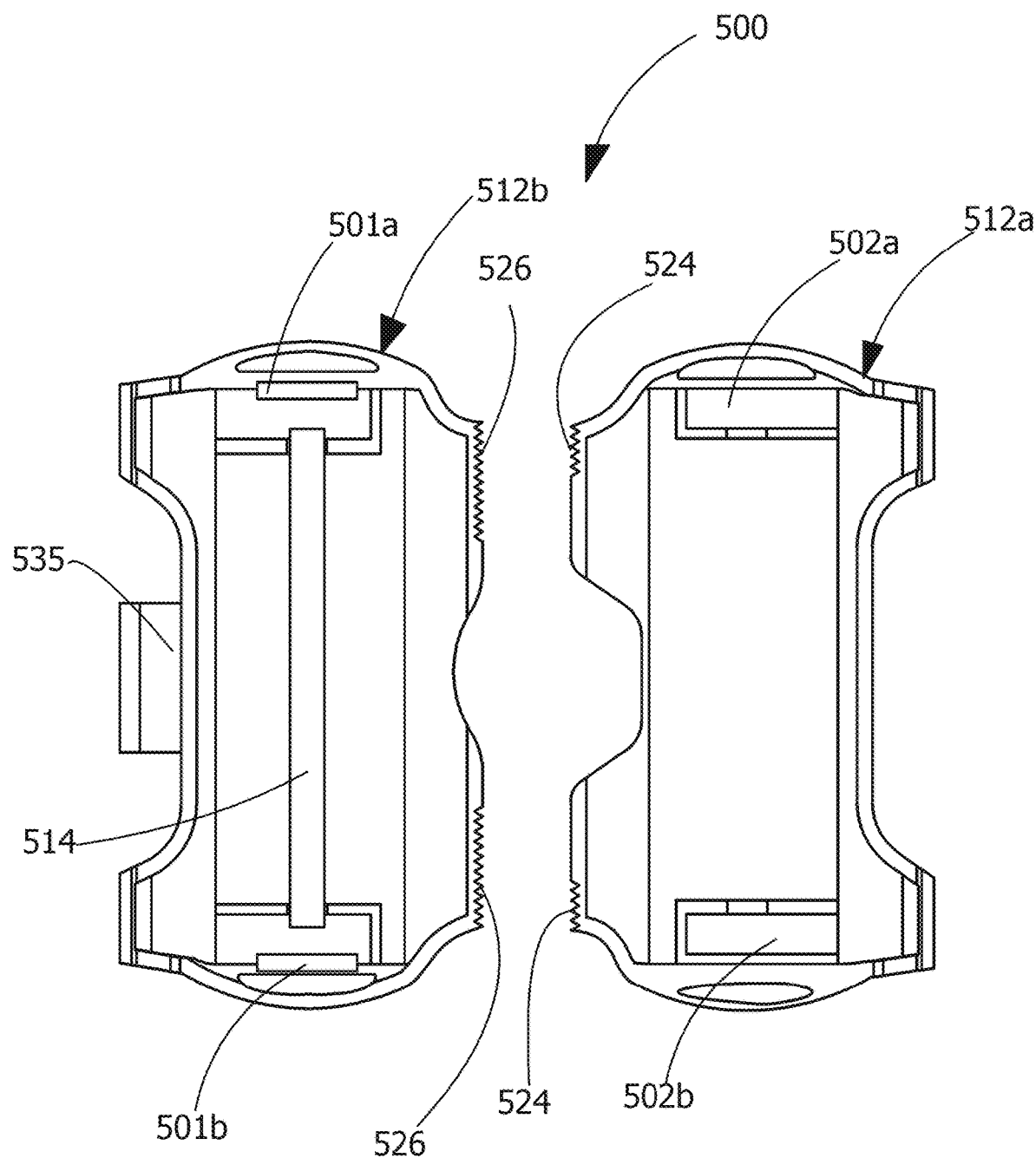
FIG. 25 is an exploded view of the dispenser apparatus of FIG. 20.

The housing 512 includes a dispensing opening 516, shown in FIG. 3, through which the wipes 520 can be pulled through. The dispensing opening 16 is located on the housing 512 about 180 degrees from the attachment members 530, 540, and curved member 535. The dispensing opening 516 is defined by a dispensing lip section 519 formed on the housing 512 and extending outwardly therefrom. The lip section 519 comprises first and second spaced apart edge sections 524, 526, as shown in FIGS. 22 and 24. The edge sections 524, 526 are substantially parallel to each other and define a slit 525 sized to receive one of the packaged applicator wipes 520 there through. The edge sections 524, 526 are partially serrated to facilitate tearing of the wipes 520, as shown in FIGS. 22, 24 and 25.

First and second cut away sections 528, 529 are formed in the housing 512. The first cut away section 528 is substantially "U" shaped and in communication with the first edge section 524, as shown in FIG. 25. The second cut away section 529 is substantially "U" shaped and in communication with the second edge section 526, as shown in FIG. 24. Preferably, the first cut away section 528 is substantially deeper than the second cut away section 529. The first cut away 528 section provides an exposed area that exposes the first applicator wipe 520 of the roll 521 of applicator wipes 520 contained in the housing 512. The second cut away section 529 provides a smaller exposed area. The first exposed area provides an opening where a user can place a finger, such as a thumb, onto the lead off applicator wipe 520, and the second exposed area allows the user to place another finger, such as the user's index finger, onto the opposite side of the lead off wipe 520, and the user can pull the lead off wipe 520 out of the housing 512 through the slit 516.

When a single wipe 520 has been pulled fully out of the housing 512, the user can tear it against the serrated edges 524, 526, thereby separating it off from the rest of the roll of wipes 521 remaining within the housing 512. The edge sections 524, 526 provide stable surfaces against which the wipe 520 can be torn using only one hand. This results in a single wipe 520 that is detached from the remaining connected wipes 520, with its packaging opened and ready for use. The serrations formed on the edge sections 524, 526 can form jagged teeth that facilitate the tearing of the wipes 520.

The housing 512 can hold multiple pre-packaged wipes 520 perforated together in a single line and rolled onto the rolling member 514 that dispenses upon a person physically pulling a wipe 520 from the housing 512 and breaking the perforated tabs manually.

Figure 26:
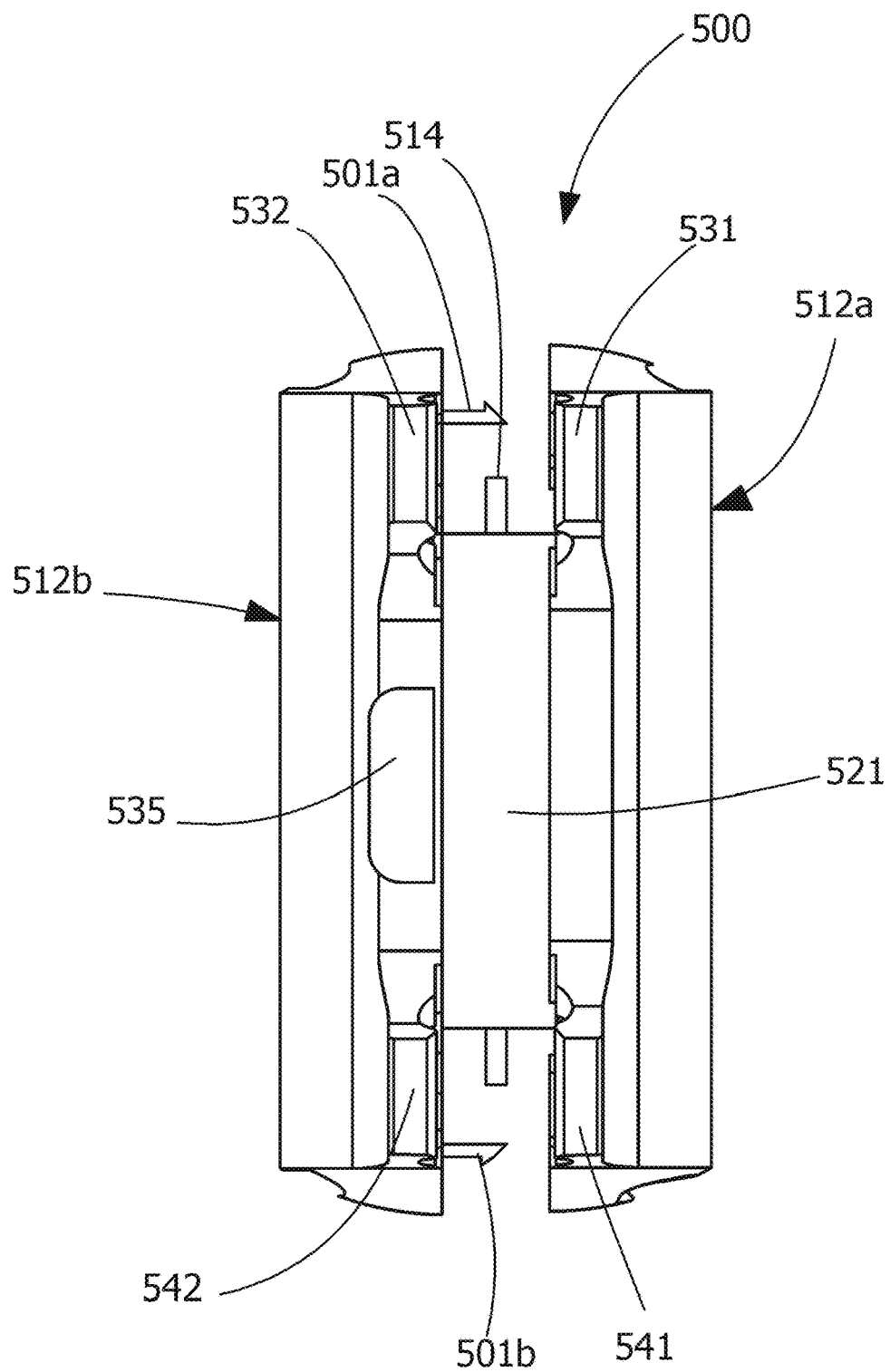
FIG. 26 is another exploded view of the dispenser apparatus of FIG. 20.
Figure 27:
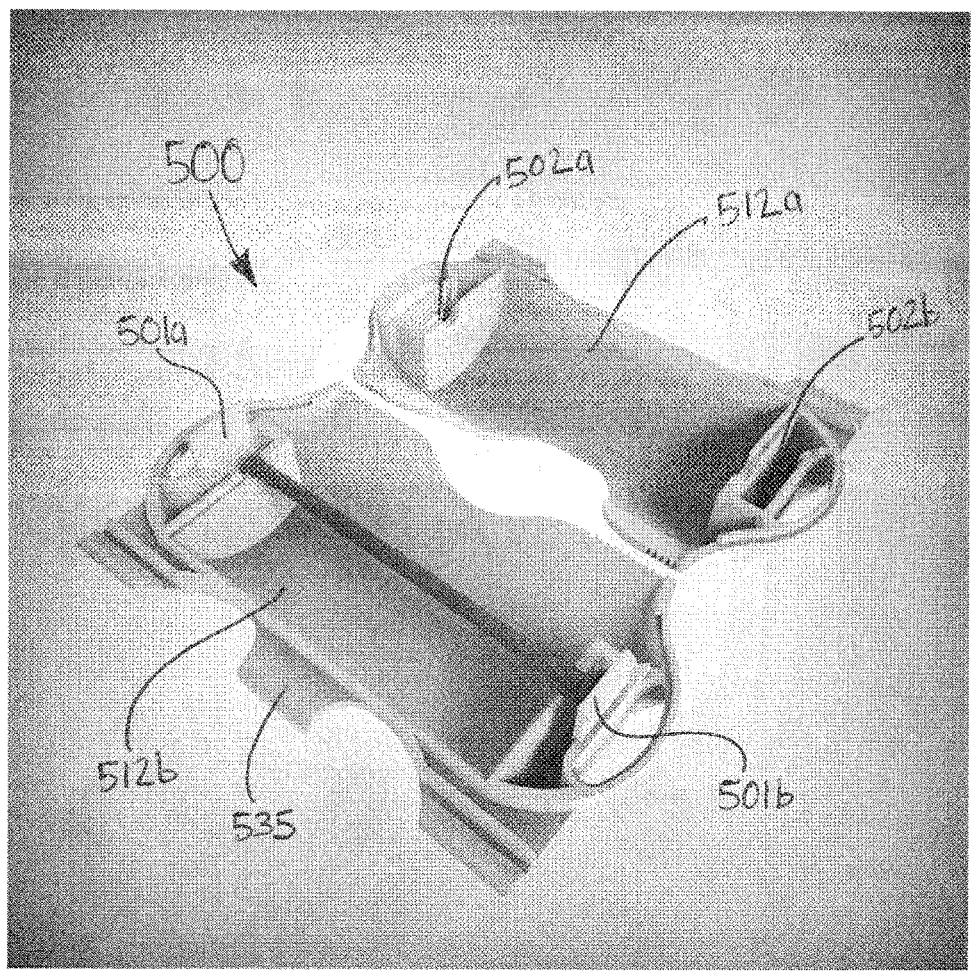
FIG. 27 is another exploded view of the dispenser apparatus of FIG. 20.

Preferably, the apparatus 500 is a disposable, one-time use unit that is discarded when all wipes 520 within the housing 512 have been used. The housing 512 can be integrally molded as a single unitary piece. Alternatively, the housing 512 can be comprised of a pair of complementary housing body sections 512a, 512b, as shown in FIGS. 25 and 27. A pair of tabs 501a, 501b are positioned at opposite longitudinal ends of one housing body section 512b, and extends outwardly from the interior of the housing body section 512b, as shown in FIGS. 25 and 27. A pair of complementary cavities 502a, 502b are formed at opposite longitudinal ends of the interior of the other housing body section 512a, as shown in FIGS. 25 and 27. To assemble the apparatus 500, a roll of wipes 521 is positioned on the rod 514, and the housing body sections 512a, 512b are positioned together, such that the tabs 501a, 501b of housing body section 512b are inserted into the cavities 502a, 502b, respectively, of housing body section 512a, as shown in FIGS. 25-27. When the tabs 501a, 501b are inserted into the cavities 502a, 502b, the angled top portions of the tabs 501a, 501b snaps into and engages structural members inside the cavities 502a, 502b, thereby locking the housing body sections 512a, 512b together. At this point, the tabs 501a, 501b are caught in housing body section 512a, and housing body section 512b cannot be pulled apart from housing body section 512a (without seriously damaging the apparatus 500 making it unusable). As such, when all wipes 520 on the roll have been used, the apparatus 500 is discarded.

The apparatus 500 can be used for every patient with an initial IV placement connected to an IV bag and tubing, and other applications as per the discretion of the healthcare professional. The dispenser apparatus 500 can be referred to and marketed as an "I-Wipe". The outside packaging of the pre-packaged wipes 520 can be labeled with "I-Wipe". Either portions or the entirety of the housing 512 and the packaging of the wipes 520 can have a distinctively bright color, such as red, to draw attention to the healthcare professional and remind him or her to stop, disinfect, inject. For patient advocacy purposes, there can also be other items with "I-Wipe" printed on them to reinforce the message to the healthcare providers of the importance of wiping ports and other sterilizing applications.

The dispenser apparatus 500 allows convenient access to alcohol wipes for the healthcare professional on IV tubing to reduce the risk of infection and increase productivity. The apparatus 500 supplies disinfecting wipes 520 and provides a more convenient and hard stop reminder for healthcare professionals to think about the safe IV infusion practice of wiping the port for fifteen seconds prior to injecting a medication. The apparatus 500 can also be used for sterilization applications other than IV infusion.

While embodiments of the invention are described above as being used to dispense sanitizing wipes for use in the medical field, the invention is not so limited. Embodiments of the invention described above can dispense a variety of applicator wipes adapted for applying a variety of substances, such as insect repellent, sunscreen, aloe, moisturizing creams, lens cleaner, nail polish remover/acetone, cuticle oil, perfume, essential oils, makeup remover, shampoo, hair oil, hair gel, dish soap, deodorant, and personal lubricant. Also, the invention is not limited to use with wipes and the like. Embodiments of the invention described above can be used to dispense a variety of packaged items, such as blotting papers, clothing refreshers and condoms.

A dispenser apparatus and method of using same are described above. Various changes can be made to the invention without departing from its scope. The above description of embodiments and best mode of the invention are provided for the purpose of illustration only and not limitation—the invention being defined by the claims and equivalents thereof.

What is claimed is:

1. An apparatus for dispensing a plurality of applicator wipes comprising:
   (a) a generally cylindrical housing adapted for containing a roll of applicator wipes, the housing having a dispensing opening formed therein whereby an applicator wipe contained in the housing can be grasped and pulled out of the housing;
   (b) first and second attachment members extending outwardly from the housing and adapted for receiving and frictionally engaging a cylindrical intravenous tubing line, wherein each of the first and second attachment members comprise first and second separated segments each having a concave surface and a slanted surface in communication with the concave surface, wherein the concave surface of the first segment faces the concave surface of the second segment and together define an arcuate cavity that is shaped and sized to receive and frictionally engage the intravenous tubing line, and the slanted surface of the first segment and the slanted surface of the second segment define a narrowing passageway wherein distance between the first segment and the second segment is greatest at a position distal to the concave surfaces of the first segment and the second segment and gradually decreases until the slanted surface of the first segment meets the concave surface of the first segment and the slanted surface of the second segment meets the concave surface of the second segment, and wherein each of the first and second attachment members has a shape as shown at reference numeral 30 in FIG. 5; and (c) a curved member positioned intermediate the first and second attachment members and adapted for moving the intravenous tubing line at an angle relative to the first and second attachment members, the curved member having an arcuate shape conforming to the cylindrical intravenous tubing line whereby the curved member can engage the intravenous tubing line without impeding a flow of fluid through the tubing line.

2. The apparatus according to claim 1, further comprising a rolling mechanism positioned within an interior space of the housing and adapted for facilitating rotation of the roll of applicator wipes.

3. The apparatus according to claim 2, wherein the housing defines first and second opposed longitudinal ends, and the rolling mechanism comprises a rod positioned in a first cavity positioned proximate the first end of the housing and a second cavity positioned proximate the second end of the housing.

4. The apparatus according to claim 1, wherein the dispensing opening is defined by a dispensing lip extending outwardly from the housing, the dispensing lip comprising a first edge section and a second edge section in spaced apart relation and substantially parallel to the first edge section, the first and second edge sections defining a slit sized to receive a single applicator wipe there through.

5. The apparatus according to claim 4, wherein the first edge section and the second edge section are at least partially serrated.

6. The apparatus according to claim 4, wherein the dispensing opening is further defined by a first cut away section formed in the housing, the first cut away section in communication with the first edge section and defining a first exposed area of the housing adapted for receiving a first finger of a user, and a second cut away section formed in the housing, the second cut away section in communication with the second edge section and defining a second exposed area of the housing adapted for receiving a second finger of a user.

7. The apparatus according to claim 1, wherein the housing includes first and second opposed longitudinal ends, the first attachment member positioned proximate the first longitudinal end and the second attachment member positioned proximate the second longitudinal end.

8. The apparatus according to claim 7, wherein the curved member is positioned equidistance between the first and second attachment members.

9. The apparatus according to claim 8, wherein the first and second attachment members are linearly aligned on the housing and positioned 180 degrees from the dispensing opening.

10. A dispensing apparatus comprising:

(a) a generally cylindrical housing adapted for containing a roll of applicator wipes;

(b) first and second attachment members extending outwardly from the housing and adapted for receiving and frictionally engaging an intravenous tubing line, wherein each of the first and second attachment members comprises first and second arcuate segments each having a concave surface and a slanted surface in communication with the concave surface, wherein the concave surface of the first segment faces the concave surface of the second segment and together define an arcuate cavity that is shaped and sized to receive and frictionally engage the intravenous tubing line, and the slanted surface of the first segment and the slanted surface of the second segment define a narrowing passageway wherein distance between the first segment and the second segment is greatest at a position distal to the concave surfaces of the first segment and the second segment and gradually decreases until the slanted surface of the first segment meets the concave surface of the first segment and the slanted surface of the second segment meets the concave surface of the second segment, and wherein each of the first and second attachment members has a shape as shown at reference numeral 30 in FIG. 5; and (c) a dispensing opening formed in the housing through which an applicator wipe contained in the housing can be grasped and pulled out of the housing, the dispensing opening comprising a first edge section and a second edge section in spaced apart relation, the first edge section and the second edge sections defining a slit sized to receive a single applicator wipe there through.

11. The dispensing apparatus according to claim 10, wherein the housing defines first and second opposed longitudinal ends, and further comprising a rotatable rod positioned in a first cavity positioned proximate the first end of the housing and a second cavity positioned proximate the second end of the housing, wherein the rotatable rod supports the roll and facilitates rotation of the roll.

12. The dispensing apparatus according to claim 10, wherein the dispensing opening is further defined by a first cut away section and a second cut away section formed in the housing, the first cut away section in communication with the first edge section and defining a first exposed area exposing one of the applicator wipes contained within the housing, whereby a user can place a first finger on said one of the applicator wipes, the second cut away section in communication with the second edge section and defining a second exposed area exposing said one of the applicator wipes contained within the housing, whereby a user can place a second finger on said one of the applicator wipes.

13. The dispensing apparatus according to claim 10, wherein the housing defines first and second opposed longitudinal ends, and further comprising a first eyelet positioned on the housing proximate the first longitudinal end and a second eyelet positioned on the housing proximate the second longitudinal end, and a fastening device containing a retractable cord, wherein the retractable cord is attached to the first eyelet.

14. The apparatus according to claim 10, wherein the first edge section and the second edge section of the dispensing opening are at least partially serrated to facilitate tearing of the single applicator wipe.

15. A disposable dispensing apparatus comprising:
(a) a generally cylindrical housing adapted for containing a roll of applicator wipes and comprising a first body section and a second body section, wherein the first body section comprises a tab member extending outwardly from an interior surface of the first body section, and the second body section comprises a recessed section adapted to receive and engage the tab member whereby the first body section and the second body section cannot be separated;
(b) a dispensing opening formed in the housing and adapted for dispensing the applicator wipes; and
(c) first and second attachment members extending outwardly from the housing and adapted for attachment to a cylindrical intravenous tubing line, wherein each of the first and second attachment members comprises first and second arcuate segments each having a concave surface and slanted surface in communication with the concave surface, wherein the concave surface of the first segment faces the concave surface of the second segment and together define an arcuate cavity that is shaped and sized to receive and frictionally engage the intravenous tubing line, and the slanted surface of the first segment and the slanted surface of the second segment define a narrowing passageway wherein distance between the first segment and the second segment is greatest at a position distal to the concave surfaces of the first segment and the second segment and gradually decreases until the slanted surface of the first segment meets the concave surface of the first segment and the slanted surface of the second segment meets the concave surface of the second segment, and wherein each of the first and second attachment members has a shape as shown at reference numeral 30 in FIG. 5.

16. The disposable dispensing apparatus according to claim 15, wherein the dispensing opening comprises a first edge section and a second edge section in spaced apart relation and substantially parallel to the first edge section, the first and second edge sections defining a slit sized to receive a single applicator wipe there through, and further wherein the first edge section and the second edge section are at least partially serrated.

17. The disposable dispensing apparatus according to claim 15, wherein the first and second attachment members are positioned proximate opposed longitudinal ends of the housing, and further comprising a curved member positioned intermediate the first and second attachment members and adapted for moving the intravenous tubing line at an angle relative to the first and second attachment members.

18. The disposable dispensing apparatus according to claim 17, wherein the curved member has an arcuate shape conforming to the cylindrical intravenous tubing line whereby the curved member can engage the intravenous tubing line without impeding a flow of fluid through the tubing line.

* * * * *